(12) United States Patent
Brimhall et al.

(10) Patent No.: US 7,713,256 B2
(45) Date of Patent: May 11, 2010

(54) SYSTEM AND METHOD OF DELIVERING LOCAL ANESTHESIA

(75) Inventors: Greg L. Brimhall, West Jordan, UT (US); Larry Partika, Bridgewater, NJ (US); Michael S. Ferrara, Wyckoff, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 235 days.

(21) Appl. No.: 11/697,903

(22) Filed: Apr. 9, 2007

(65) Prior Publication Data

US 2007/0250037 A1 Oct. 25, 2007

Related U.S. Application Data

(62) Division of application No. 10/682,848, filed on Oct. 10, 2003, now abandoned.

(60) Provisional application No. 60/417,728, filed on Oct. 10, 2002.

(51) Int. Cl.
*A61M 31/00* (2006.01)
*A61M 5/178* (2006.01)

(52) U.S. Cl. .................. 604/512; 604/164.02

(58) Field of Classification Search .......... 604/164.01, 604/164.02, 164.04, 164.07, 16, 4.08, 165.01, 604/165.02, 167.01–167.05, 158, 161, 164.06, 604/164.11, 164.09, 278, 239, 93.01, 43, 604/44, 512, 21, 20; 606/34, 41; 607/3, 607/46, 116, 6; 600/373, 424, 427, 547, 600/26

See application file for complete search history.

(56) References Cited

U.S. PATENT DOCUMENTS

| 2,522,052 A | 9/1950 | Logan et al. |
| 3,087,486 A | 4/1963 | Kilpatrick |
| 3,098,813 A | 7/1963 | Beebe et al. |

(Continued)

FOREIGN PATENT DOCUMENTS

EP 0102538 A1 3/1984

(Continued)

OTHER PUBLICATIONS

Non-Final Office Action in U.S. Appl. No. 11/697,916, (Jun. 16, 2009), 8 pgs.

(Continued)

*Primary Examiner*—Kevin C Sirmons
*Assistant Examiner*—Catherine N Witczak
(74) *Attorney, Agent, or Firm*—Diehl Servilla LLC

(57) ABSTRACT

A catheter and introducer needle assembly is provided including a catheter adapter at its proximal end. The catheter adapter includes a side port in fluid communication with the catheter and a septum located in the proximal end of the catheter adapter proximal of the side port. The introducer needle is connected at its proximal end to a needle hub and includes at least one notch in communication with the introducer needle lumen. The notch allows blood to flow into the open distal end of the needle and through the notch into the catheter lumen (specifically, the annular space between the outside of the introducer needle and the inside of the catheter and catheter adapter). Thereafter, the blood can flow through the annular space and then through the side port and extension tube that extends from the catheter adapter.

13 Claims, 22 Drawing Sheets

U.S. PATENT DOCUMENTS

| | | | |
|---|---|---|---|
| 3,249,103 A | 5/1966 | Woodhouse |
| 3,352,306 A | 11/1967 | Hirsch |
| 3,682,162 A | 8/1972 | Colyer |
| 3,828,780 A | 8/1974 | Morrison, Jr. |
| 3,943,932 A | 3/1976 | Woo |
| 4,128,173 A | 12/1978 | Lazarus et al. |
| 4,301,802 A | 11/1981 | Poler |
| 4,411,266 A | 10/1983 | Cosman |
| 4,644,960 A | 2/1987 | Johans |
| 4,755,170 A | 7/1988 | Golden |
| 4,810,248 A | 3/1989 | Masters et al. |
| 4,816,024 A | 3/1989 | Sitar et al. |
| 4,824,433 A | 4/1989 | Marz et al. |
| 4,832,696 A | 5/1989 | Luther et al. |
| 4,834,718 A | 5/1989 | McDonald |
| 4,846,811 A | 7/1989 | Vanderhoof |
| 4,917,669 A | 4/1990 | Bonaldo |
| 4,929,241 A | 5/1990 | Kulli |
| 4,944,725 A | 7/1990 | McDonald |
| 4,964,854 A | 10/1990 | Luther |
| 4,978,344 A | 12/1990 | Dombrowski et al. |
| 4,994,041 A | 2/1991 | Dombrowski et al. |
| 5,007,902 A * | 4/1991 | Witt ............................ 604/117 |
| 5,049,136 A | 9/1991 | Johnson |
| 5,051,109 A | 9/1991 | Simon |
| 5,053,017 A | 10/1991 | Chamuel |
| 5,085,648 A | 2/1992 | Purdy |
| 5,135,504 A | 8/1992 | McLees |
| 5,147,327 A | 9/1992 | Johnson |
| 5,186,712 A | 2/1993 | Kelso et al. |
| 5,215,525 A | 6/1993 | Sturman |
| 5,215,528 A | 6/1993 | Purdy et al. |
| RE34,416 E | 10/1993 | Lemieux |
| 5,279,591 A | 1/1994 | Simon |
| 5,300,045 A | 4/1994 | Plassche, Jr. |
| 5,312,359 A | 5/1994 | Wallace |
| 5,322,517 A | 6/1994 | Sircom et al. |
| 5,328,482 A | 7/1994 | Sircom et al. |
| 5,330,434 A | 7/1994 | McFarlane |
| 5,395,347 A | 3/1995 | Blecher et al. |
| 5,409,461 A | 4/1995 | Steinman |
| 5,433,739 A | 7/1995 | Sluijter et al. |
| 5,458,658 A | 10/1995 | Sircom |
| 5,512,052 A | 4/1996 | Jesh |
| 5,558,651 A | 9/1996 | Crawford et al. |
| 5,562,633 A | 10/1996 | Wozencroft |
| 5,573,510 A | 11/1996 | Isaacson |
| 5,584,809 A | 12/1996 | Gaba |
| 5,584,818 A | 12/1996 | Morrison |
| 5,599,310 A | 2/1997 | Bogert |
| 5,601,536 A | 2/1997 | Crawford et al. |
| 5,605,539 A | 2/1997 | Buelna et al. |
| 5,611,781 A | 3/1997 | Sircom et al. |
| 5,613,952 A | 3/1997 | Pressly, Sr. et al. |
| 5,630,802 A * | 5/1997 | Moellmann et al. ..... 604/164.01 |
| 5,662,610 A | 9/1997 | Sircom |
| 5,676,658 A | 10/1997 | Erskine |
| 5,683,365 A | 11/1997 | Brown et al. |
| 5,695,474 A | 12/1997 | Daugherty |
| 5,697,907 A | 12/1997 | Gaba |
| 5,697,914 A * | 12/1997 | Brimhall ...................... 604/177 |
| 5,704,919 A | 1/1998 | Kraus et al. |
| 5,713,876 A | 2/1998 | Bogert et al. |
| 5,807,395 A | 9/1998 | Mulier et al. |
| 5,833,670 A | 11/1998 | Dillon et al. |
| 5,853,393 A | 12/1998 | Bogert |
| 5,865,806 A | 2/1999 | Howell |
| 5,879,337 A | 3/1999 | Kuracina et al. |
| 5,882,337 A | 3/1999 | Bogert et al. |
| 5,911,705 A | 6/1999 | Howell |
| 5,935,109 A | 8/1999 | Donnan |
| 5,951,515 A | 9/1999 | Osterlind |
| 5,976,110 A * | 11/1999 | Greengrass et al. ......... 604/158 |
| 6,001,080 A | 12/1999 | Kuracina et al. |
| 6,004,294 A | 12/1999 | Brimhall |
| 6,012,213 A | 1/2000 | Chang et al. |
| 6,117,108 A | 9/2000 | Woehr et al. |
| 6,146,380 A | 11/2000 | Racz et al. |
| 6,159,185 A | 12/2000 | Tanihata |
| 6,190,370 B1 | 2/2001 | Tsui |
| 6,298,256 B1 | 10/2001 | Meyer |
| 6,352,521 B1 * | 3/2002 | Prosl ..................... 604/167.03 |
| 6,456,874 B1 | 9/2002 | Hafer et al. |
| 6,485,475 B1 | 11/2002 | Chelly |
| 2001/0056275 A1 | 12/2001 | Brushey |

FOREIGN PATENT DOCUMENTS

| | | |
|---|---|---|
| EP | 0 747 083 A2 | 11/1996 |
| EP | 0 747 085 A2 | 11/1996 |
| EP | 0 750 916 A2 | 2/1997 |
| EP | 1205156 A2 | 5/2002 |
| GB | 20/88215 A | 10/1994 |
| GB | 2 343 118 A | 9/1999 |
| RU | 1391626 A1 | 4/1998 |
| WO | WO 94/23784 A1 | 10/1994 |
| WO | WO 98/57689 | 6/1997 |
| WO | WO 98/19725 | 10/1997 |
| WO | WO 99/08742 | 8/1998 |
| WO | WO 00/06226 | 8/1999 |
| WO | WO 02/45786 A3 | 6/2002 |
| WO | WO 2004/032995 A3 | 4/2004 |

OTHER PUBLICATIONS

Product Profiles Plexus Anesthesia (3 pages from website: www.bbraunusa.com/stimpulex/contiplex.html—Nov. 14, 2002).

PNA Medical Systems—Continuous Plexus Sets (5 pages from website: www.pnamed.com/continuous.html— Nov. 14, 2002).

New Paediatric Regional Anaesthesia Product Range—B. Braun Melsungen AG (2 pages).

* cited by examiner

SYSTEM AND METHOD OF DELIVERING LOCAL ANESTHESIA

RELATED APPLICATIONS

This application is a divisional application of U.S. Ser. No. 10/682,848 filed Oct. 10, 2003, which claims benefit under 35 U.S.C. §119(e) from U.S. Provisional Patent Application No. 60/417,728, filed on Oct. 10, 2002, the entire content of which is incorporated herein by reference.

BACKGROUND OF THE INVENTION

1. Field of Invention

This invention relates to systems and methods of delivering anesthesia to tissue. Specifically, the invention relates to systems and methods of providing anesthesia to tissue using a catheter and introducer needle assembly, and applying a current to the needle assembly to create stimulation in the tissue to identify a target needle depth at which to deliver the anesthesia. The present application 2. Description of the Related Art In certain instances, it is desirable to provide anesthesia at a point in a patient's tissue proximate to a nerve. Such procedures are known as peripheral block procedures. Typically, the clinician employs a hollow needle that is coated with an electrical insulator, leaving only the tip of the needle exposed. The clinician first locates anatomical landmarks to establish the location of the nerve. As the needle is inserted into the tissue, a small electric current is passed through the needle. The current passes to the patient's tissue at the tip of the needle (the only exposed portion of the needle) and causes surrounding muscle tissue to contract or "twitch." This twitching is observed by the clinician and helps locate the needle tip. As the needle tip proceeds closer to the nerve, the clinician reduces the current and moves the needle tip to a point that is believed to be appropriately close to the nerve to be effective.

Once the needle tip is in place, the clinician delivers a bolus of anesthesia through the needle to the region around the nerve. Typically, such a delivery of anesthesia will deaden both the motor and sensory impulses. After delivery of the anesthesia, the rigid needle is withdrawn. Consequently, if more anesthesia is required, another needle must be inserted. Alternatively, some practitioners will insert a catheter through the needle so that the tip of the catheter is near the tip of the needle. The needle is then withdrawn over the catheter and the catheter remains in place. After the needle is threaded off the catheter, a special connector is attached to the catheter end to permit that delivery of additional anesthesia. This can be a time consuming process.

SUMMARY OF THE INVENTION

It is an aspect of one implementation of the invention to provide a system and method for delivering anesthesia via a needle while providing a catheter for delivery of additional anesthesia over time.

It is an aspect of another implementation of the invention to provide a device and method adapted for delivering anesthesia to tissue via both a needle and a catheter, at the election of the clinician.

It is an aspect of yet another implementation of the invention to provide a system and method for locating the tip of the needle within the patient's tissue before delivering anesthesia or withdrawing the needle.

In accordance with one implementation of the invention, a catheter and introducer needle assembly is provided including a catheter adapter at its proximal end, which preferably includes at least one wing radially extending from the catheter adapter. The catheter adapter also includes a side port in fluid communication with the catheter. A septum is located in the proximal end of the catheter adapter proximal of the side port. Preferably, the septum prevents any fluid from flowing into or out of the proximal end of the catheter adapter and thus diverts any fluid flowing in the catheter lumen into the side port. Similarly, the septum diverts any fluid flowing from the side port into the catheter lumen. The septum has a hollow interior portion to minimize drag on the introducer needle as it is being withdrawn from the catheter through the septum.

The introducer needle is connected at its proximal end to a needle hub and preferably includes at least one notch, i.e., a hole or opening in the sidewall, formed therein in communication with the introducer needle lumen (or "central bore"). The notch is formed in the introducer needle such that fluid can flow between the central bore of the needle and the catheter adapter. When delivering anesthesia through the needle, anesthesia fluid is delivered through the extension tube to the side port. From the side port, the fluid enters the catheter adapter and proceeds either directly through the notch, or travels in the annular space between the needle and the catheter, and then through the notch (depending on the position of the notch along the needle). Passing through the notch, the fluid passes through the central bore and out of the tip of the needle. As shown, the notch may be positioned near the tip of the needle within the catheter. The notch can also be positioned elsewhere and still practice aspects of the invention. For example, the notch may be positioned on the needle within the catheter adapter aligned with the side port, as discussed in U.S. Pat. No. 5,935,110, incorporated herein by reference, to encourage flow through the needle.

It will be appreciated that this structure permits the flow of liquid through the side port to either the annular space between the needle and the catheter (or a notch that may positioned on the needle within the catheter adapter), through the notch into the lumen within the needle, and out of the tip of the needle. When the needle is removed, the catheter adapter remains in place, permitting later delivery of fluids through the catheter. Access to the side port may be through a closed system access port, thereby ensuring that an open conduit to the environment is not created.

In accord with certain implementations of the invention, an electrical connection may be provided to the needle via the needle hub. A hand-held, battery powered device may be connected to the electrical connection, thereby providing an appropriate charge. The needle may be made of an electrically conductive material, such as stainless steel. The catheter, however, is made of a material that acts as an electrical insulator. Therefore, only the tip of the needle carries the electrical charge to the patient's tissue. As the clinician inserts the catheter assembly into the patient's tissue, an electrical charge may be delivered through the needle to the tissue. Certain tissue will respond to the electrical charge by twitching. Specifically, muscles will contract under an electrical charge. Consequently, the clinician can use this information, along with other indicia, to determine the location of the tip of the needle during insertion. After the clinician confirms proper placement of the catheter assembly into the patient's tissue, the clinician delivers liquid anesthesia to that tissue by supplying the anesthesia to the side port of the catheter assembly. Preferably, the clinician delivers the anesthesia using a syringe attached to the extension tube. The clinician then withdraws the introducer needle from the catheter by pulling the needle hub in a proximal direction. The septum should be long enough so that both the notch and the open distal end of the introducer needle can be located simultaneously within the septum, such as described in U.S. Pat. No. 6,506,181, incorporated herein by reference. This ensures no blood or anesthesia leakage occurs when the introducer needle is being withdrawn from the catheter. If the septum is too short, the open distal end of the introducer needle could be distal of the distal end of the septum in the fluid flow path while the notch could be located proximal of the proximal end of the septum. This could allow fluid to leak from the catheter when the introducer needle is being withdrawn.

During infusion of the anesthetic, it is desirable that a clinician be able to aspirate though the device to assure that the needle point is not accidentally located within an artery (which anatomically is very near the target nerves). The need to aspirate is so that a clinician can determine if the device is in the venous system prior to infusing significant amounts of anesthetic, which could result in a very detrimental result if infused into the venous system. If the device accidentally penetrates an artery, during aspiration blood would be drawn through the needle point, out through the notch in the needle, and visualized in the annular space between the needle and the catheter and all fluid connection locations proximal of the notch (i.e. catheter adapter and extension tubing) if the notch is located near the distal end of the needle. If the notch is located in the catheter adapter the aspirated blood would be visualized in the clear/translucent catheter adapter and points proximal of the notch located within the catheter adapter.

Once the needle is withdrawn, the catheter remains in place, with the tip of the catheter disposed in the tissue being anesthetized. Over time, the clinician may determine that additional anesthesia needs to be applied. In such case, the clinician operably connects a source of anesthesia to the fluid access device on the extension tube. The fluid anesthesia passes through the extension tube, into the catheter adapter and into the catheter itself. The fluid anesthesia then passes through the catheter lumen into the patient's tissue.

DETAILED DESCRIPTION OF THE PREFERRED EMBODIMENTS

As used herein, the term "proximal" refers to a location with respect to the device that, during normal use, is closest to the clinician using the device and farthest from the patient in connection with whom the device is used. Conversely, the term "distal" refers to a location with respect to the device that, during normal use, is farthest from the clinician using the device and closest to the patient in connection with whom the device is used.

As used herein, the term "top", "up" or "upwardly" refers to a location with respect to the device that, during normal use, is radially away from the longitudinal axis of the device and away from the patient's skin. Conversely, as used herein, the term "bottom", "down" or "downwardly" refers to a location with respect to the device that, during normal use, is radially away from the longitudinal axis of the device and toward the patient's skin, As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

Figure 1:
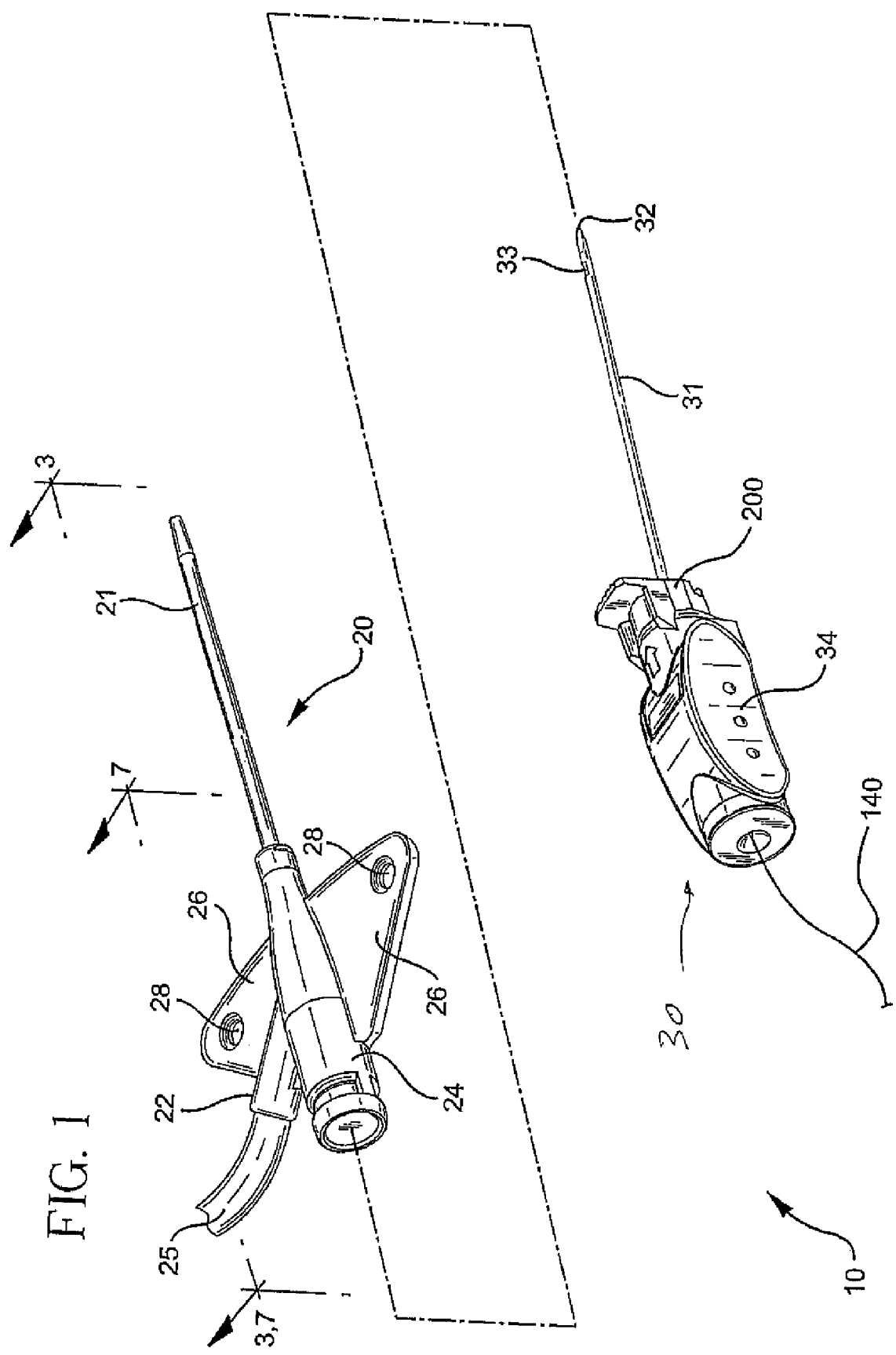
FIG. 1 is a perspective view of an integrated catheter and introducer needle for use in accordance with an aspect of this invention.
Figure 2:
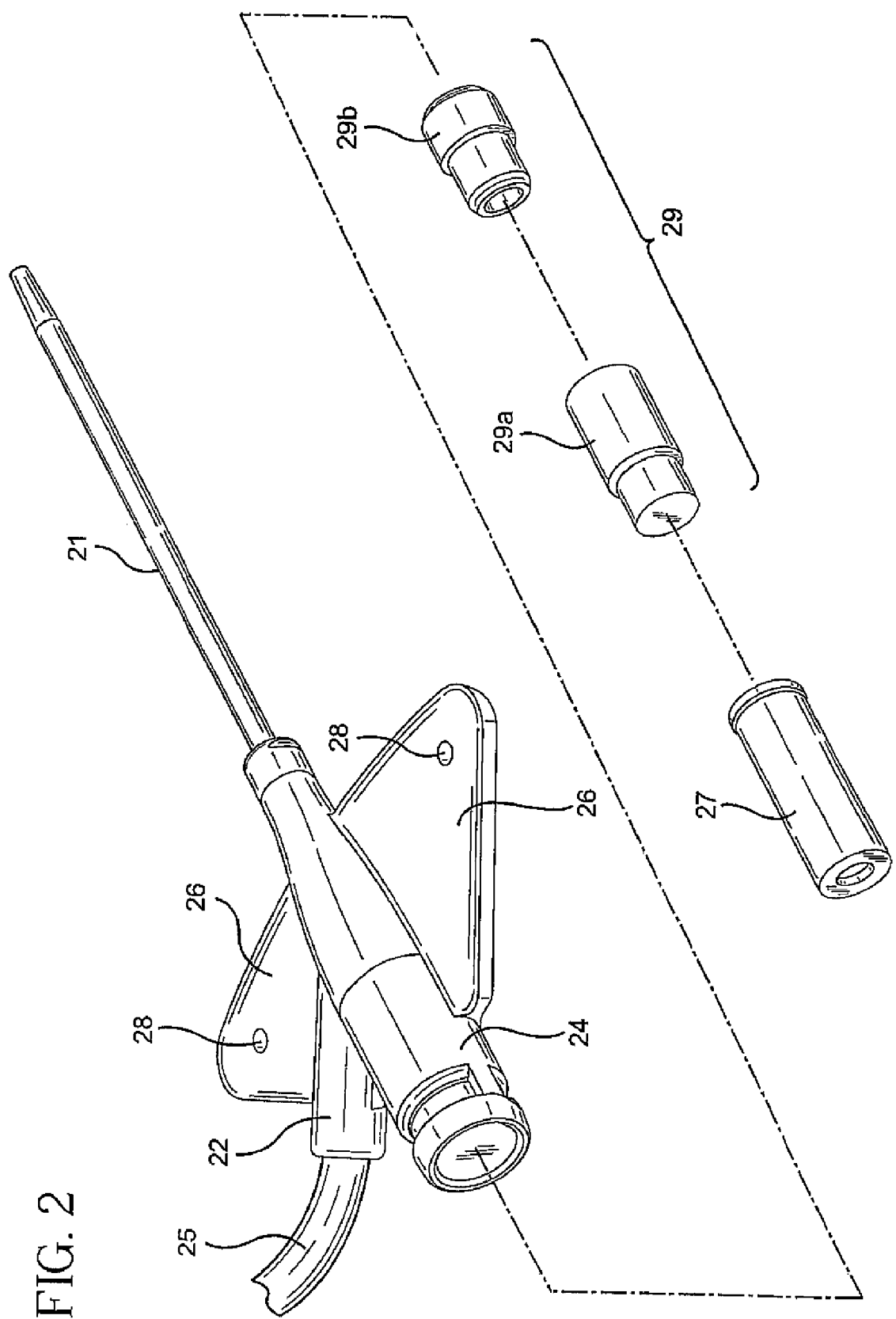
FIG. 2 is an exploded perspective view of an integrated catheter assembly of FIG. 1.

An integrated catheter and introducer needle assembly is shown generally at 10 in FIG. 1. The catheter and introducer assembly may be configured as described in U.S. patent application Ser. No. 09/865,918, incorporated herein by reference. Of course, other assemblies may be used and practice aspects of the invention, such as the assembly described in U.S. patent application Ser. No. 09/717,148, incorporated herein by reference. Specifically, the catheter and introducer assembly may include a shield 200 or other device designed to capture the tip of the needle as it is withdrawn from the assembly, as disclosed in U.S. patent application Ser. No. 09/717,148, incorporated herein by reference. Further details of a catheter and introducer assembly can be also found in U.S. patent application Ser. No. 09/590,600 and in WO 01/93940, the entire contents of both of these documents being incorporated herein by reference.

As shown, the catheter assembly 20 includes catheter 21 affixed to catheter adapter 24. Suitable materials for catheter 21 include, but are not limited to, thermoplastic resins such as fluorinated ethylene propylene (FEP), polytetrafluoroethylene (PTFE), polyurethane and the like. The catheter 21 is formed from a thermoplastic hydrophilic polyurethane that softens with exposure to physiological conditions present in the patient's body. Importantly, the catheter is preferably made of a material that does not occlude during use and that acts as an electric insulator. The electric insulation characteristic of the catheter material should be such that the electric charge passing through the needle, discussed below, does not pass through the catheter to the patient's tissue. In addition, the material used to form catheter 21 may be transparent or at least translucent to reduce visual interference with the clinician. The catheter material should also be selected so that it does not interact with the intended liquid anesthesia. Suitable materials for catheter adapter 24 include, but are not limited to, thermoplastic polymeric resins such as polycarbonate, polystyrene, polypropylene and the like. The material used to form catheter adapter 24 may be transparent or at least translucent to allow the clinician to view the flow of anesthesia there through.

Catheter adapter 24 includes a side port 22, which has an extension tube 25 connected thereto. Extension tube 25 is preferably formed from a translucent material such as polyvinyl chloride, polyurethane and the like to facilitate visualization of the anesthesia through extension tube 25. The proximal end 127 of extension tube 25 may include a closed-system access port, such as luer lock adaptor 126. The closed system-access port may include the needleless luer access connector as shown in FIGS. 19-22 and disclosed in U.S. Pat. No. 6,171,287, incorporated herein by reference, or other fluid access device to allow the connection of an anesthesia or other IV fluid supply line to extension tube 25. Preferably, the closed system access port is designed to receive a luer lock, luer slip or other connector. The closed system access port may also be a PRN adapter. In any event, it is desirable that the port maintain a seal against the environment until accessed by a syringe tip or other device.

Specifically, as shown in FIGS. 19-22, the needleless luer access connector includes a housing 410 having a top portion 412 and bottom portion 416. Typically plastic materials such as polycarbonate, or PETG could be used to form housing 410. Housing 410 defines an inlet 411 and an outlet 417 with a cavity or bore 413 extending therebetween. Inlet 411 is defined at the top of top portion 412 and outlet 417 is defined at the bottom of bottom portion 416 of the needleless luer access connector. Inlet 411, and thus that portion of bore 413 adjacent to inlet 411 and that portion of top portion 412 adjacent to inlet 411, must be sized and configured in conformity with at least some of the International Standards Organization (ISO) standards for a female luer connection. This will allow a male luer slip or lock to be connected to inlet 411. Thus, inlet 411 has a maximum external diameter of about 0.265 inches (6.73 millimeters) and an internal diameter of about 0.214 inches (5.44 millimeters) to allow a male luer taper to extend into inlet 411. The exterior of the top of top portion 412 includes luer threads 414 that allow another medical device having a male luer lock to be connected to the top of proximal portion 412. Alternatively, no luer threads 414 need be formed on the exterior of the top of top portion 412 so that another medical device having a male luer slip can be connected to the top of top portion 412. Outlet 417, and thus that portion of bore 413 adjacent to outlet 417 is sized and configured as a male luer taper that complies with the ISO standards for a male luer taper. ISO standard 594-2:1986(E) requires that the male luer taper have a minimum length of about 0.2953 inches (7.5 millimeters). Forming this part of housing 410 in accordance with ISO standards allows the needleless luer access connector of this invention to be connected to a standard female luer configuration of another medical device. If desired, a luer lock collar 416a may be formed about the male luer taper to lock the connector to a female luer. In such a case, the luer lock should comply with ISO standards. According to ISO standards, the root diameter R of the thread on the male luer lock fitting should be about 0.315 inches (8 millimeters) and the crest diameter C of the thread on the male luer lock fitting should be about 0.276 inches (7 millimeters). In addition, the male luer taper must extend a minimum of about 0.083 inches (2.1 millimeters) past the end of luer lock collar 416a.

The top surface 415 of top portion 412 adjacent to inlet 411 transitions between two high points and two low points. Each high point is about 180 degrees apart from each other and each low point is also about 180 degrees apart from each other such that each high point is about 90 degrees from each low point. Preferably, each high point should be greater than zero but less than about 0.050 inches (1.143 millimeters) higher than each low point. Most preferably, each high point should be about 0.027 inches (0.686 millimeters) higher than each low point. To achieve a smooth circumferential top surface 415 that transitions in a smooth undulating fashion between high points and low points, top surface 415 can be formed by using a curved surface with a radius of about 0.30 inches (7.62 millimeters) as the template to cut the top of proximal portion 412. In geometric terms, an imaginary cylinder defined by the top of proximal portion 412 can be cut with an imaginary cylinder having a radius of about 0.30 inches (7.62 millimeters) oriented 90 degrees to the longitudinal axis of the imaginary cylinder defined by the top of proximal portion 412. This results in top surface 415 having the shape described. By changing the radius of the imaginary cylinder, the distance between high points and low points can be changed.

A septum 420 is located in top portion 412 of the needleless luer access connector to control fluid flow therethrough. Typically materials such as silicone or polyisoprene could be used for form septum 420. Septum 420 has an enlarged proximal portion 421, a medial portion 422 and an enlarged distal portion 423. The top of enlarged proximal portion 421 can be formed with an annular lip 424 extending about the circumference of proximal portion 421. Lip 424 provides extra mass to give enlarged proximal portion 421 extra rigidity to prevent it from folding in when it is accessed by a male luer taper. Lip 424 may also be bonded to the proximal portion of top portion 412. Medial portion 422 has a cross sectional area that is smaller than the cross sectional area of proximal portion 421 and smaller than the cross sectional area of distal portion 423. Preferably medial portion 422 has a generally oblong cross-section with a major axis M1 substantially equal to the internal diameter of inlet 411. Alternatively, the major axis may be slightly greater than the internal diameter of inlet 411 to help ensure that septum 420 remains in inlet 411. The minor axis M2 of medial portion 422 is smaller than the diameter of proximal portion 421 and smaller than the internal diameter of inlet 411. Thus, medial portion 422 has a cross-sectional area that is smaller than the cross-sectional area of inlet 411. This provides a space between the external surfaces of medial portion 422 along the major axis thereof and the sidewalls of housing 410 that define inlet 411 where the material of septum 420 can be displaced when a male luer taper is disposed in septum 420. Enlarged distal portion 423 defines an annular slot 426 extending about the bottom thereof. In addition, an enlarged diametrical portion 427 extends across the bottom of enlarged distal portion 423.

A slit 425 is formed in septum 420 and extends longitudinally through proximal portion 421, medial portion 422 and distal portion 423. As seen in the top plan view of septum 420 of FIG. 22, slit 425 has a transverse axis T and is defined by a pair of sides 425a and a pair of ends 425b. Preferably, a diametrical portion of an enlarged distal portion extends from sides 425a of slit 425 along an apex back to the bottom surface of enlarged distal portion. Diametrical portion provides increased mass adjacent to the bottom of slit 425 to help keep slit 425 closed against fluid flow.

Septum 420 is disposed in top portion 412 of housing 410 such that enlarged proximal portion 421 rests on top of top surface 415. As a result, enlarged proximal portion 421 projects above the top of inlet 411. In addition, because of the undulating configuration of top surface 415, proximal portion 421 is pushed upon along high points A. Septum 420 is aligned in housing 410 such that the middle of sides 425a of slit 425 are aligned with each of the high points and transverse axis T is aligned with the low points. Thus the minor axis of medial portion 422 is aligned with the high points and the major axis of medial portion 422 is aligned with the low points. Distal portion 423 is captured between top portion 412 and bottom portion 416 of housing 410 such that preferably the top wall of bottom portion 416 engages annular slot 26 of septum 420. The bottom wall of top portion 412 is bonded to a circumferential flange 419 formed along a medial portion of bottom portion 423 adjacent to luer lock collar 416a. If desired, an annular slot 419a can be formed in flange 419 and the bottom wall of top portion 412 can be inserted into annular slot 419a. Any standard bonding technique, such as chemical adhesive or ultrasonic welding can be used to bond top portion 412 to bottom portion 416. Preferably, medial portion 422 is held in tension when septum 420 is located in housing 410. This tension in combination with portions of proximal portion 421 being lifted up by high points A on top surface 415 results in a compressive force being exerted against sides 425a to force slit 425 closed at least at the top of proximal portion 421.

When a male luer taper of another medical device, such as a syringe, is pushed against the top of proximal portion 421 of septum 420, proximal portion 421 deflects distally and laterally and allows the male luer taper to access slit 425 in septum 420. As the male luer taper is pushed further into slit 425, medial portion 422 also deflects distally and laterally. By having a cross-section for medial portion 422 that is smaller than the cross-section of bore 413, space is provided inside bore 413 to allow such lateral deflection of medial portion 422. This distal and lateral deflection of septum 420 forces slit 425 to open and allows the male luer taper to penetrate septum 420 into slit 425. When the male luer taper is fully inserted into septum 420, slit 425 is forced open along the entire length of septum 420 and thus allows fluid to flow through septum 420 and the needleless luer access connector. Thereafter, the male luer taper of the other medical device can be withdrawn from slit 425. The inherent resiliency of septum 420 causes septum 420 to return to its normal unstressed state with slit 425 closed. This prevents any further fluid flow through septum 420.

The catheter adapter may be selectively connected to a source of anesthesia 300 via the extension tube. Such a fluid supply line can be connected to extension tube 25 prior to insertion of assembly 10 into a patient. In such case, a stopcock or Roberts clamp is provided to prevent fluid flow through the extension tube until desired. Further, a syringe may be employed as an anesthesia source to engage the luer lock adapter 126, allowing the clinician to deliver controlled doses of anesthesia using a syringe. Side port 22 is in fluid communication with the lumen of catheter 21 via the opening 122 so that fluid infused through extension tube 25 will pass into the patient once catheter 21 is properly positioned in the patient.

Catheter adapter 24 may also include a pair of wings 26 that extends radially 25 outwardly from either side of catheter adapter 24. Wings 26 are preferably located adjacent to side port 22 below the main body portion of catheter adapter 24. Wings 26 facilitate manipulation of catheter assembly 20 and enhance patient comfort when catheter assembly 20 is affixed to the patient. Wings 26 may include suture holes 28 to facilitate fixation of catheter assembly 20 to the patient. Alternatively, various adhesive systems may be employed to affix the catheter adapter to the patient's skin. The proximal end of catheter adapter 24 is sealed with a septum 29 to ensure that fluid does not leak out of the proximal end of catheter adapter 24. The septum can be a single plug bonded to the catheter adapter. Alternatively, the septum 29 may be formed from two portions, a proximal portion 29a and a distal portion 29b, each of which is pre-slit to facilitate locating an introducer needle 31 there through.

Septum distal portion 29b provides the primary seal preventing fluid flow past septum while septum proximal portion 29a provides a secondary seal. Although septum 29 could be formed from one piece, two pieces may be used because it is easier and less expensive to manufacture. In addition, forming septum 29 from two separate pieces increases the column strength and facilitates assembly into catheter adapter 1024. Preferably, septum distal portion 29b and septum proximal portion 29a are formed from the same material and have the same hardness. Suitable materials for septum 29 include a peroxide-cured elastomer such as polyisoprene, silicone and the like where the materials have a durometer in the range of 35-45 Shore A. Preferably, a septum housing 27 having an open proximal end and an open distal end surrounds at least a portion of septum proximal portion 29a and septum distal portion 29b in an interference fit to hold septum 29 in place in position in catheter adapter 24. Alternatively, septum 29 could be located in catheter adapter 24 without the use of housing 27. However, housing 27 facilitates placement of septum 29 in catheter adapter 24.

As shown in the Figures, housing 27 extends only along the proximal portion of septum distal portion 29b. However, if desired, housing 27 could extend completely along the entire length of septum 29 or just along septum distal portion 29b. With such a configuration, it is to be understood that housing 27 would be configured so it would apply the desired compressive force to septum 29 instead of catheter adapter 24 as discussed below. The open proximal and distal ends of housing 27 allow an introducer needle 31 to extend through septum 29 past housing 27. Preferably, the proximal end of housing 27 abuts and extends over a portion of the surface area of the proximal face of septum 29. This configuration prevents the attachment of another medical device to the proximal end of catheter adapter 24. Instead, any such medical device that should be connected to catheter adapter 24 would be connected to the fluid access device 126 located at the proximal end of extension tube 25.

Septum 29 and septum housing 27 are located in catheter adapter 24 so that at least the distal portion of septum distal portion 29b engages the inside of catheter adapter 24. The external diameter of at least the distal portion of septum distal portion 29b is greater than the internal diameter of catheter adapter 24 at least along the portion that engages the distal portion of septum distal portion 29b. Preferably, the external diameter of the distal portion of septum distal portion 29b should be at least 5% larger than the internal diameter of the relevant portion of catheter adapter 24. With this configuration, catheter adapter 24 exerts a radial compressive force against distal portion 29b. This compressive force helps to hold housing 27 in place and also helps to seal septum distal portion 29b after introducer needle 31 has been withdrawn from septum 29 so that septum distal portion 29b does not take a compression set about introducer needle 31. The portion of catheter adapter 24 that engages septum distal portion 29b should be arranged such that the proximal end of septum 29 is adjacent to the open proximal end of catheter adapter 24 when catheter adapter 24 engages septum distal portion 28b. Septum housing 27 and septum 29 could also be affixed inside catheter adapter 24 using an alternate technique such as by an interference fit between housing 27 and catheter adapter 24, the use of an adhesive or by ultrasonic welding.

Figure 7:
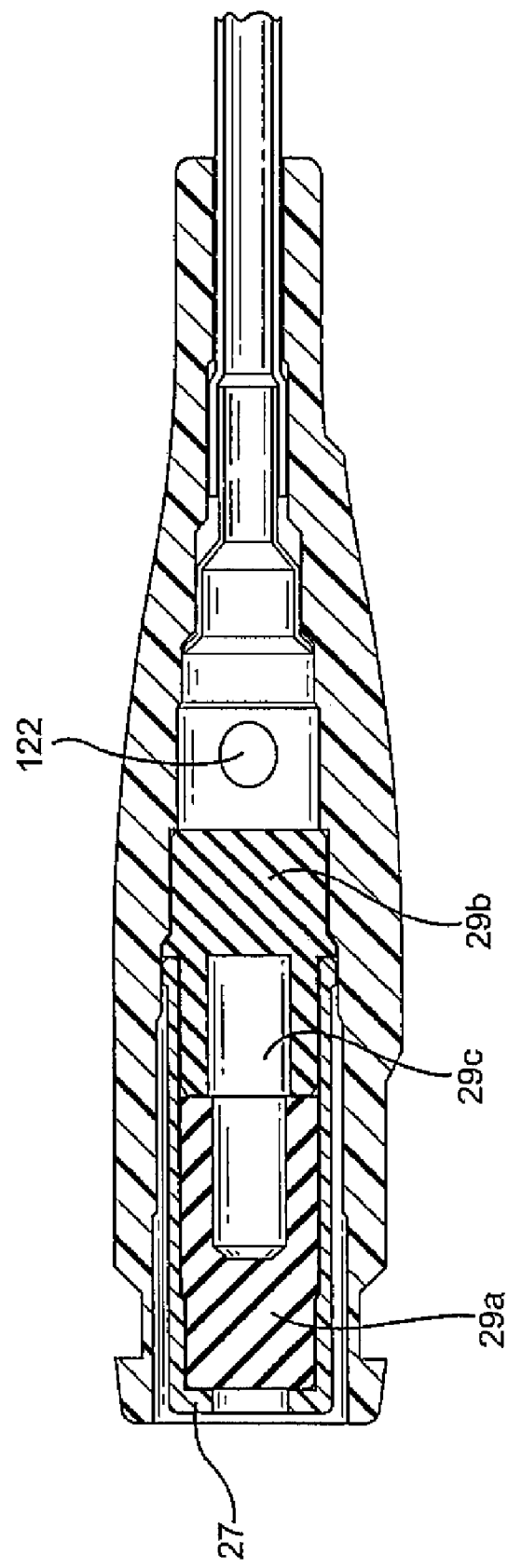
FIG. 7 is a cross-sectional view of a portion of the integrated catheter taken along line 7-7 in FIG. 1 without the introducer needle assembly.
Figure 11:
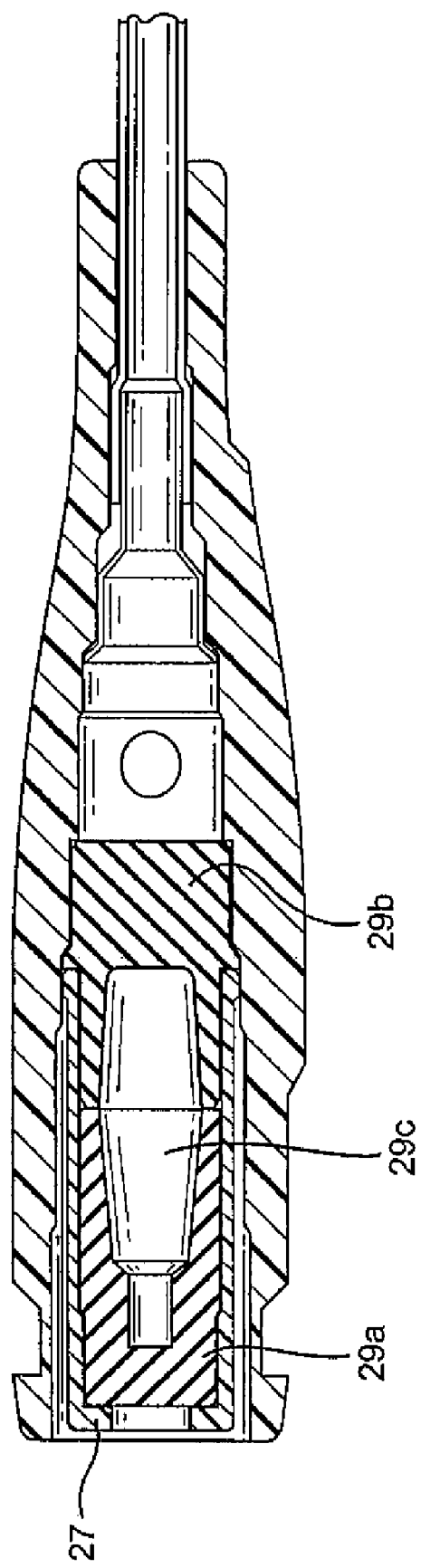
FIG. 11 is a cross-sectional view similar to the view in FIG. 7 of a portion of the integrated catheter having the low drag septum but showing the configuration of the second embodiment of the low drag septum disposed in the catheter.
Figure 12:
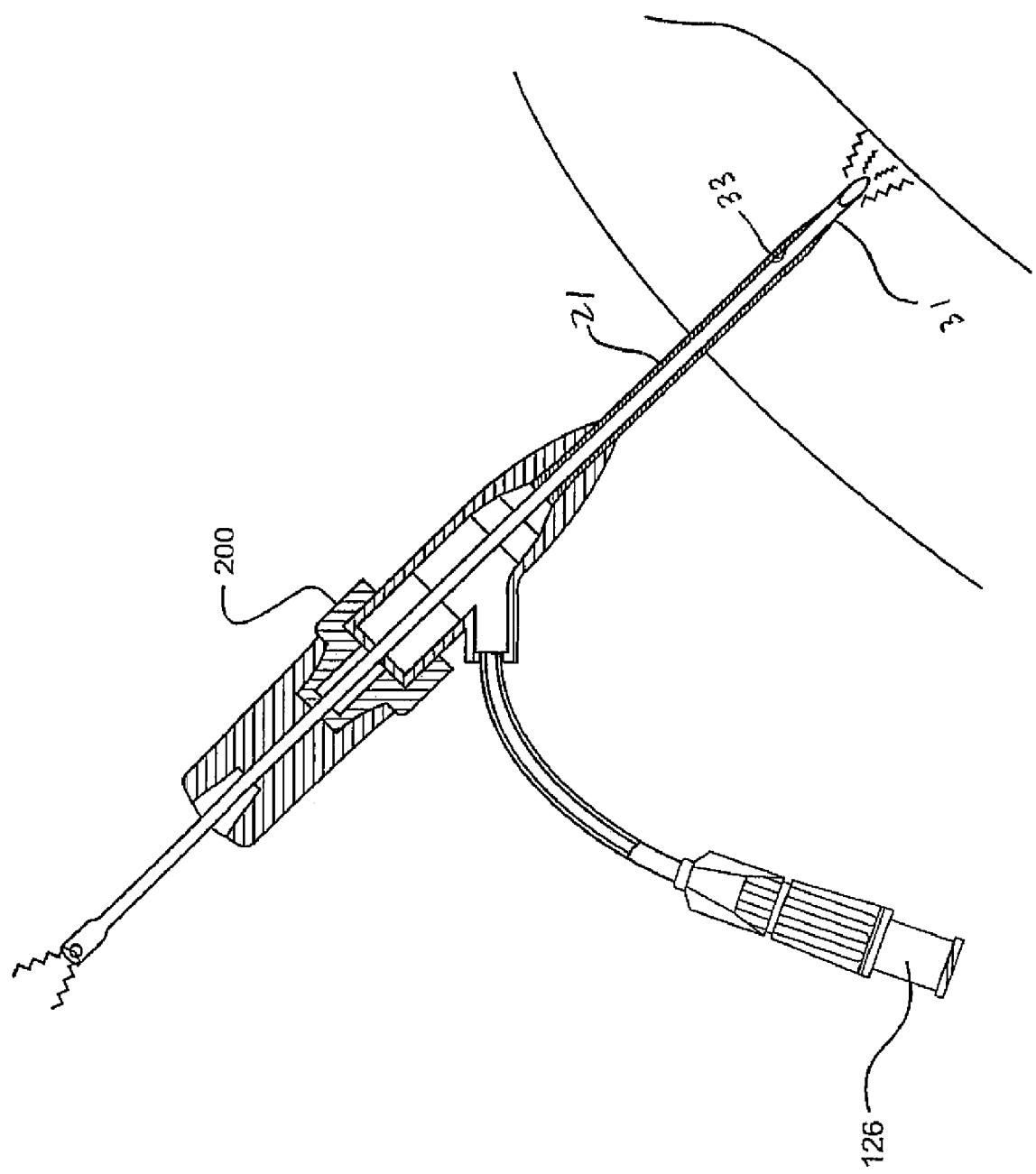
FIG. 12 is a schematic cross sectional view showing the catheter assembly inserted into a patient's tissue.
Figure 13A:
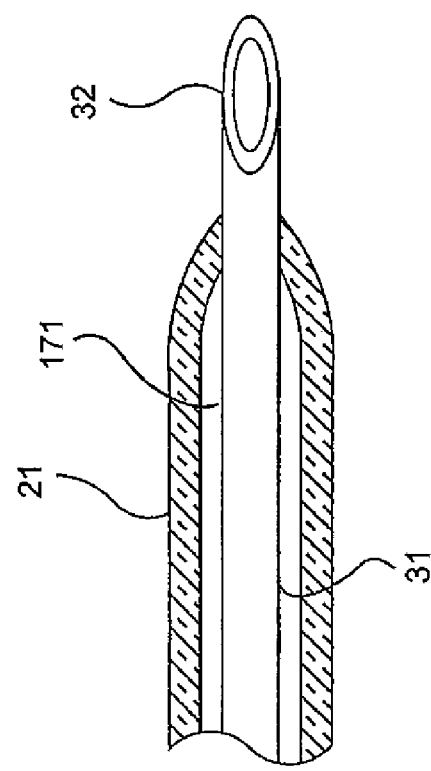
FIGS. 13A and 13B are top and side isolation views in partial cutaway showing 25 the needle tip and catheter tip.
Figure 13B:
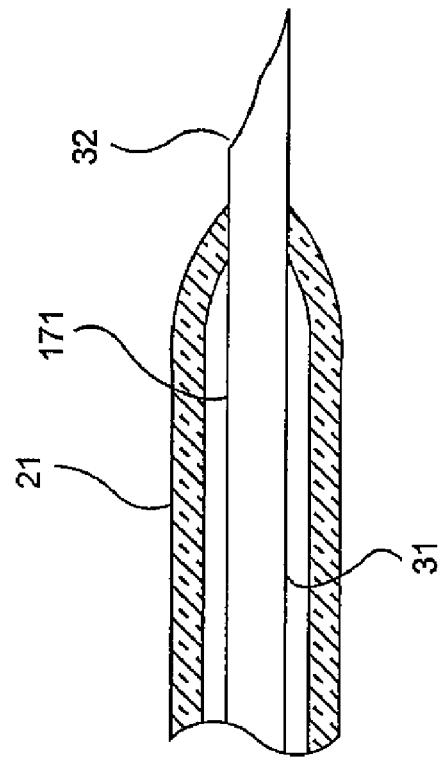
Figure 14:
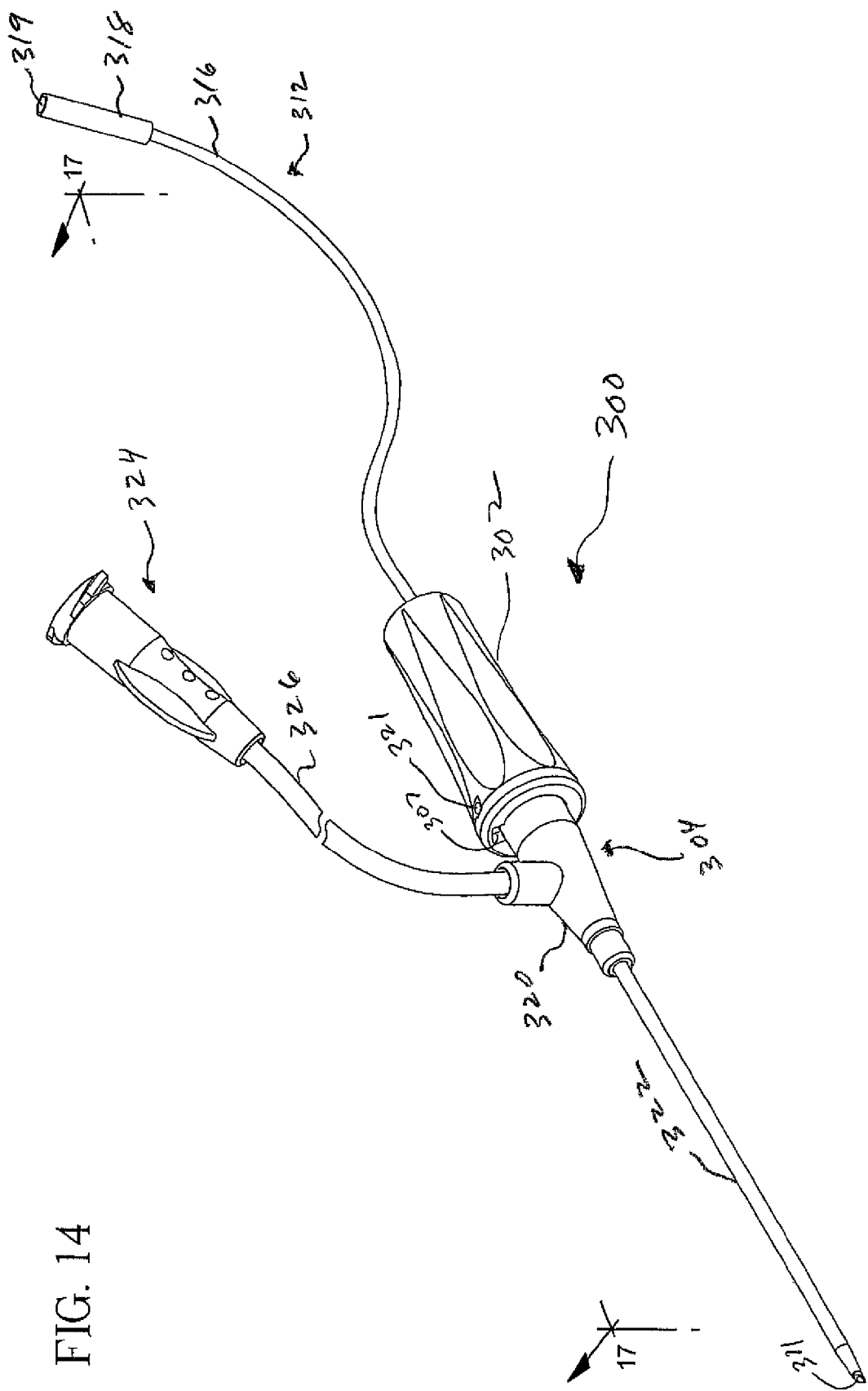
FIG. 14 is a perspective view of an integrated catheter and introducer needle for use in accordance with another aspect of this invention.
Figure 15:
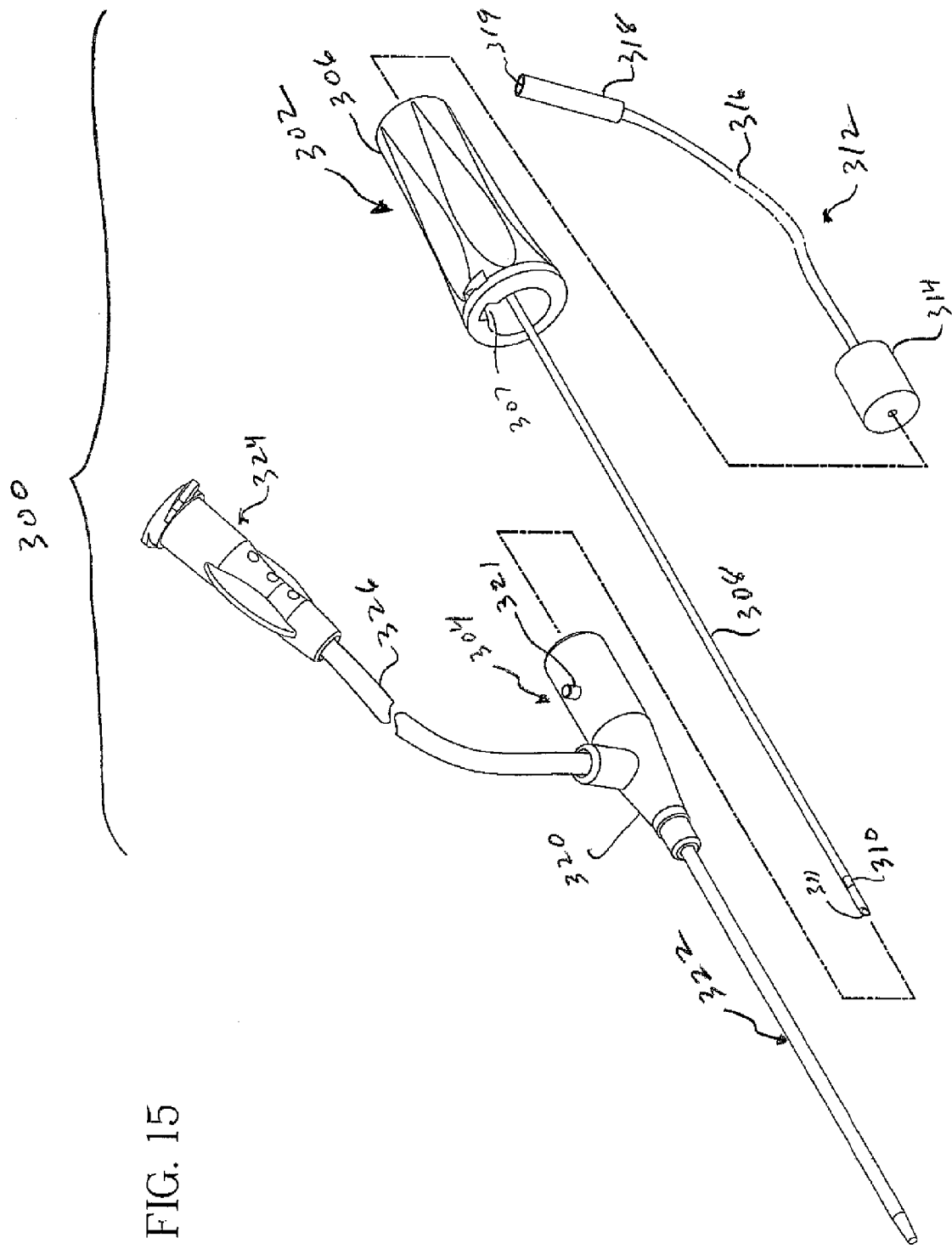
FIG. 15 is an exploded perspective view of an integrated catheter assembly of FIG. 14.
Figure 16:
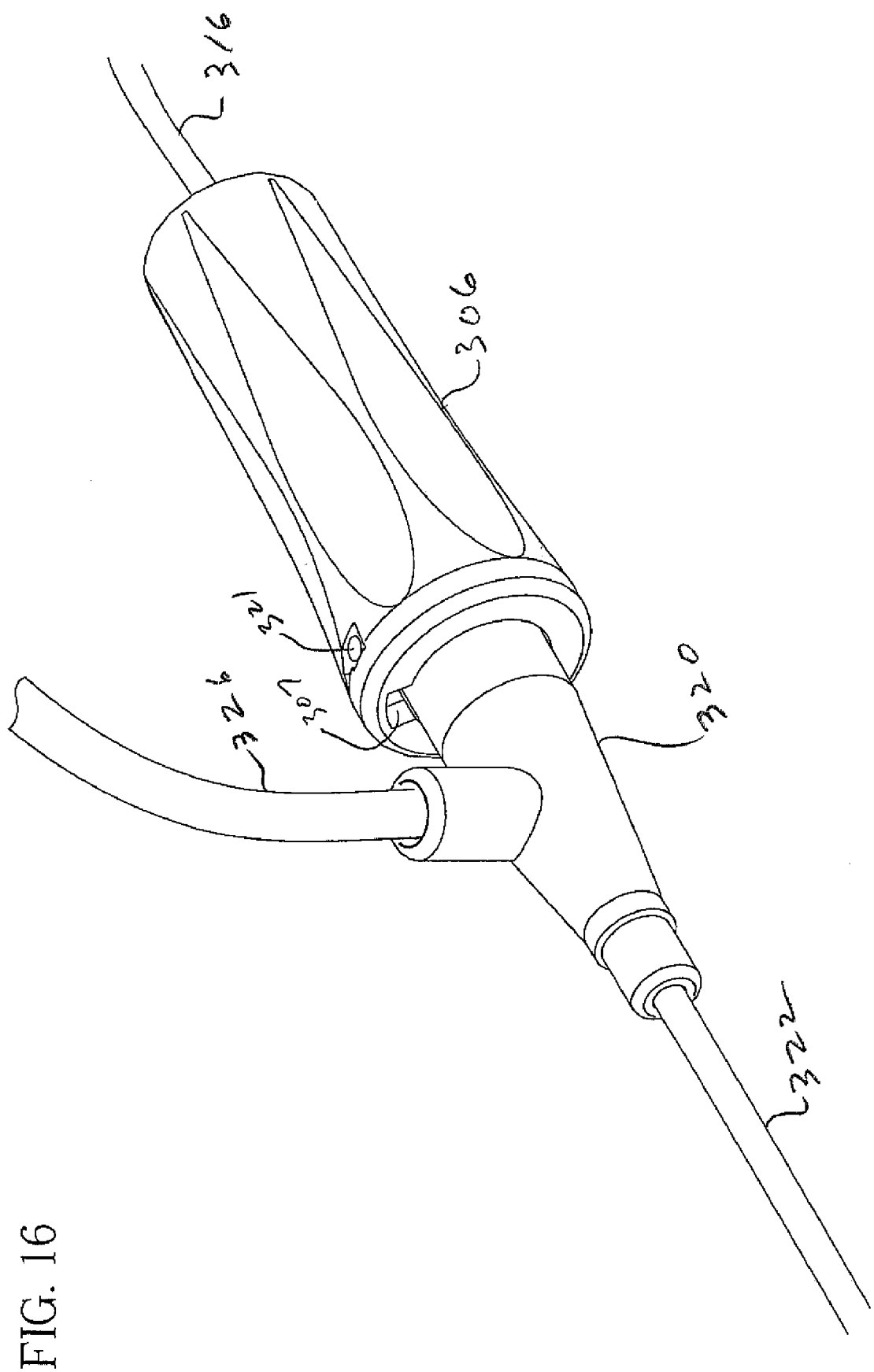
FIG. 16 is a detailed perspective view of the catheter adapter of the catheter as shown in FIG. 14.
Figure 17:
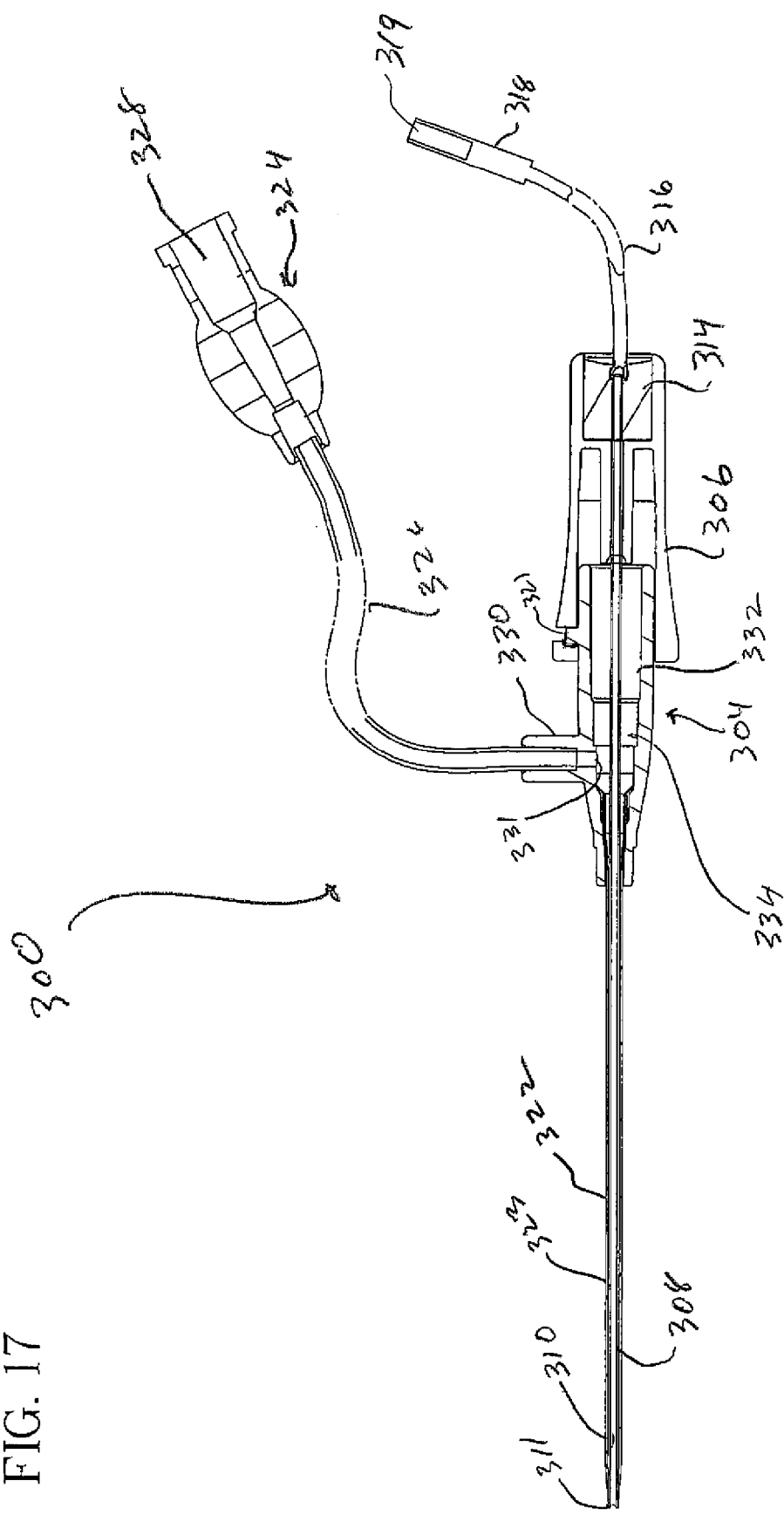
FIG. 17 is a cross-sectional view taken along line 17-17 in FIG. 14 showing the catheter and introducer needle assembly.
Figure 18:
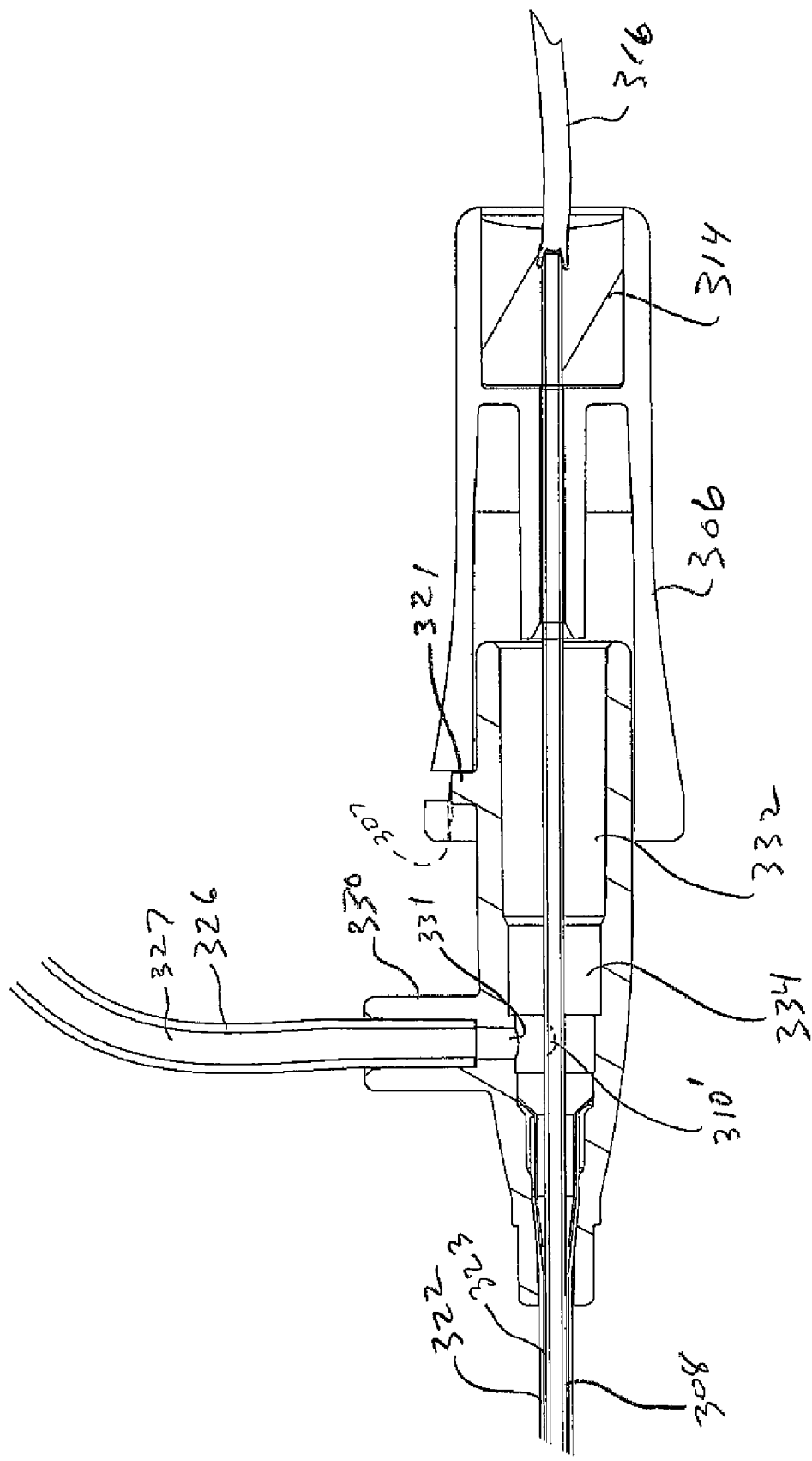
FIG. 18 is a detailed cross-sectional view of the catheter adapter shown in FIG. 16.
Figure 19:
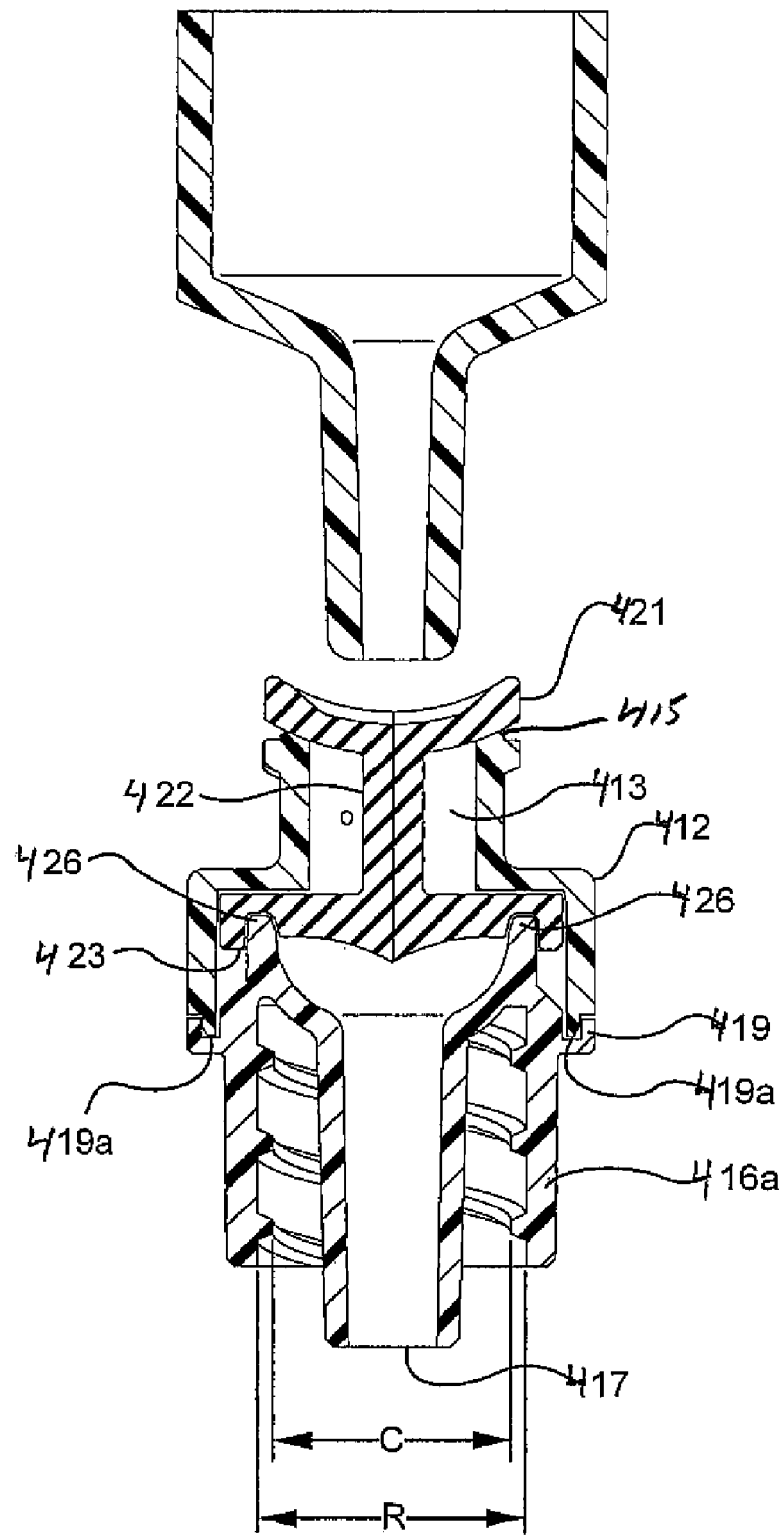
FIG. 19 is a cross-sectional view of an example of a luer lock adapter and luer lock about to engage the luer lock adapter.
Figure 20:
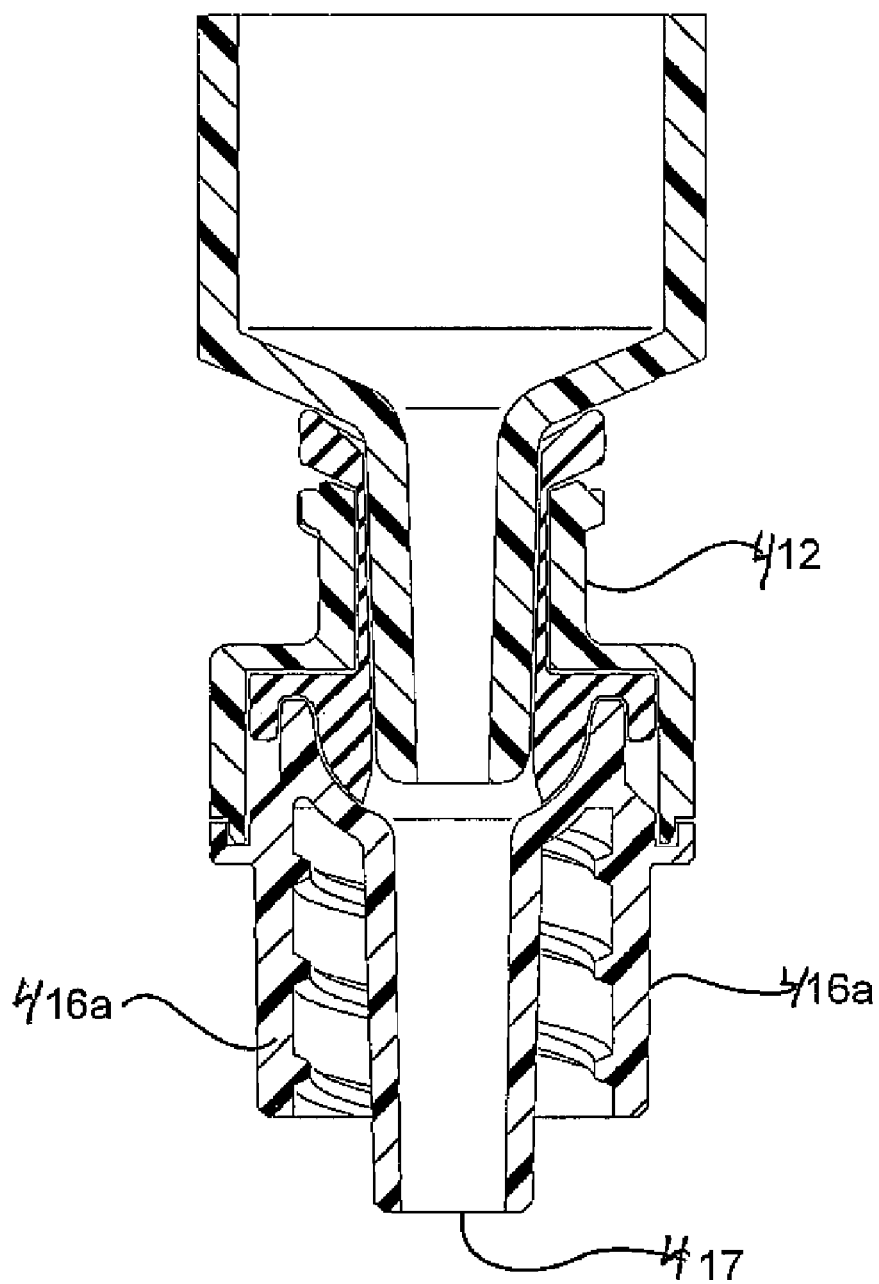
FIG. 20 is a cross-sectional view of the luer lock engaged with the luer lock adapter shown in FIG. 19.
Figure 21:
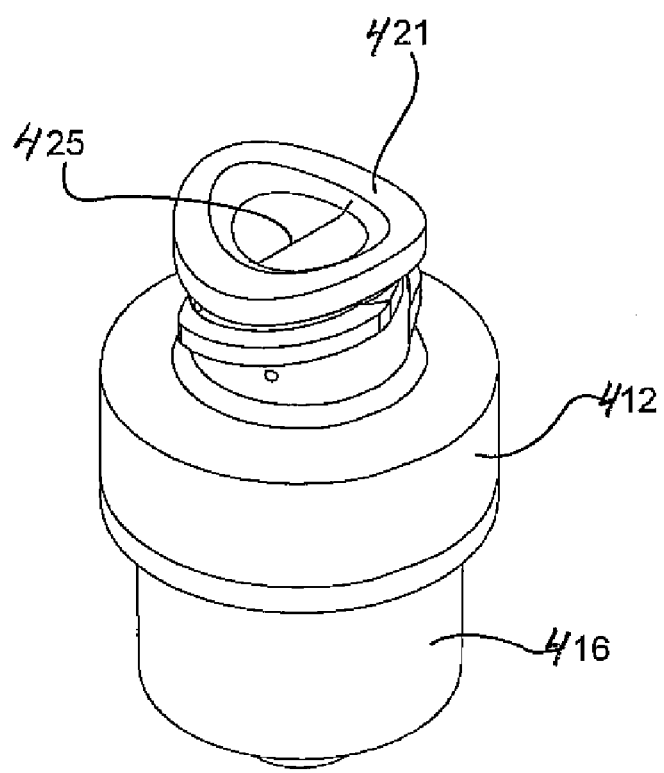
FIG. 21 is a perspective view of the luer lock adapter shown in FIG. 19.
Figure 22:
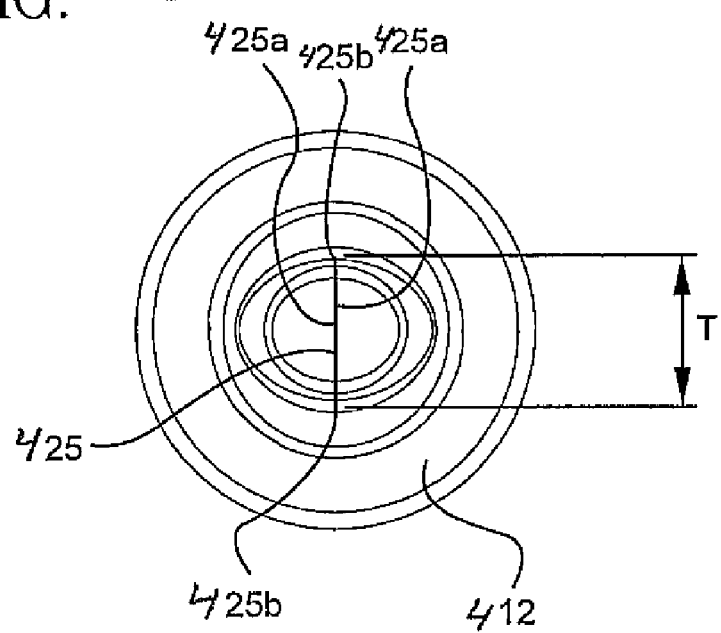
FIG. 22 is a top view of the luer lock adapter shown in FIG. 19.

Septum 29 defines a cavity or hollow interior portion 29c formed between septum proximal portion 29a and septum distal portion 29b. This minimizes drag on introducer needle 31 as it is being withdrawn from catheter assembly 20. Testing of septum 29 against a standard septum shows that the average drag force for septum 29 with hollow interior portion 29c is about 0.15 pounds while the average drag force for a septum without a hollow interior is about 0.30 pounds. Hollow interior portion 29c should be sized to minimize drag but it must not be too large so that it acts as a reservoir for microbial growth therein if fluid were to become trapped therein. Hollow interior portion 29c could have a cylindrical configuration such as shown in FIG. 7. However, preferably hollow interior portion 29c has a configuration such as shown in FIG. 11 where the proximal section is generally cylindrical, the medial section is tapered such that it increases in diameter in the distal direction, and the distal section is tapered such that it decreases in diameter in the distal direction. Preferably the taper should be between about 2 degrees and about 10 degrees to the horizontal plane. This configuration reduces the volume of dead space that could become a reservoir for blood when introducer needle 31 is withdrawn from catheter 21. Thus the cross section of hollow interior portion 29c should closely approximate the cross section of the largest needle that would be used for introducer needle 31. Preferably, hollow interior portion 29c is between about 6 and about 8 millimeters in length. If desired, hollow interior portion 29c could be filled with some material to prevent unwanted material from becoming trapped therein. If a lubricious material such as a silicone liquid or gel is disposed in hollow interior portion 29c that material could also serve to enhance the drag-reducing characteristic of septum 29.

Figure 8:
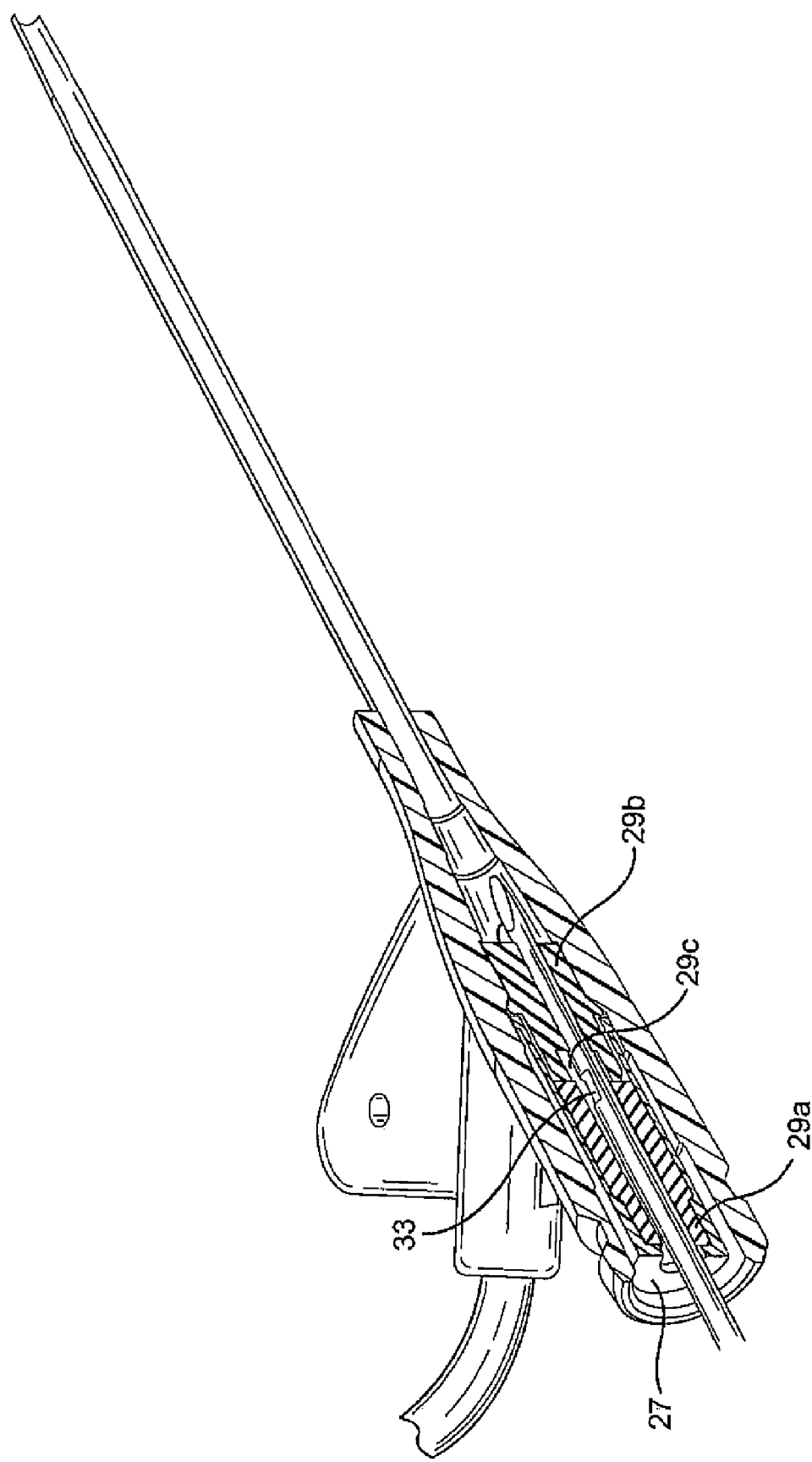
FIG. 8 is a perspective cross-sectional view of the catheter and introducer needle assembly similar to FIG. 3 but showing a different relationship between the introducer needle and the low drag septum where the distal tip of the introducer needle is distal of the distal end of the septum.
Figure 9:
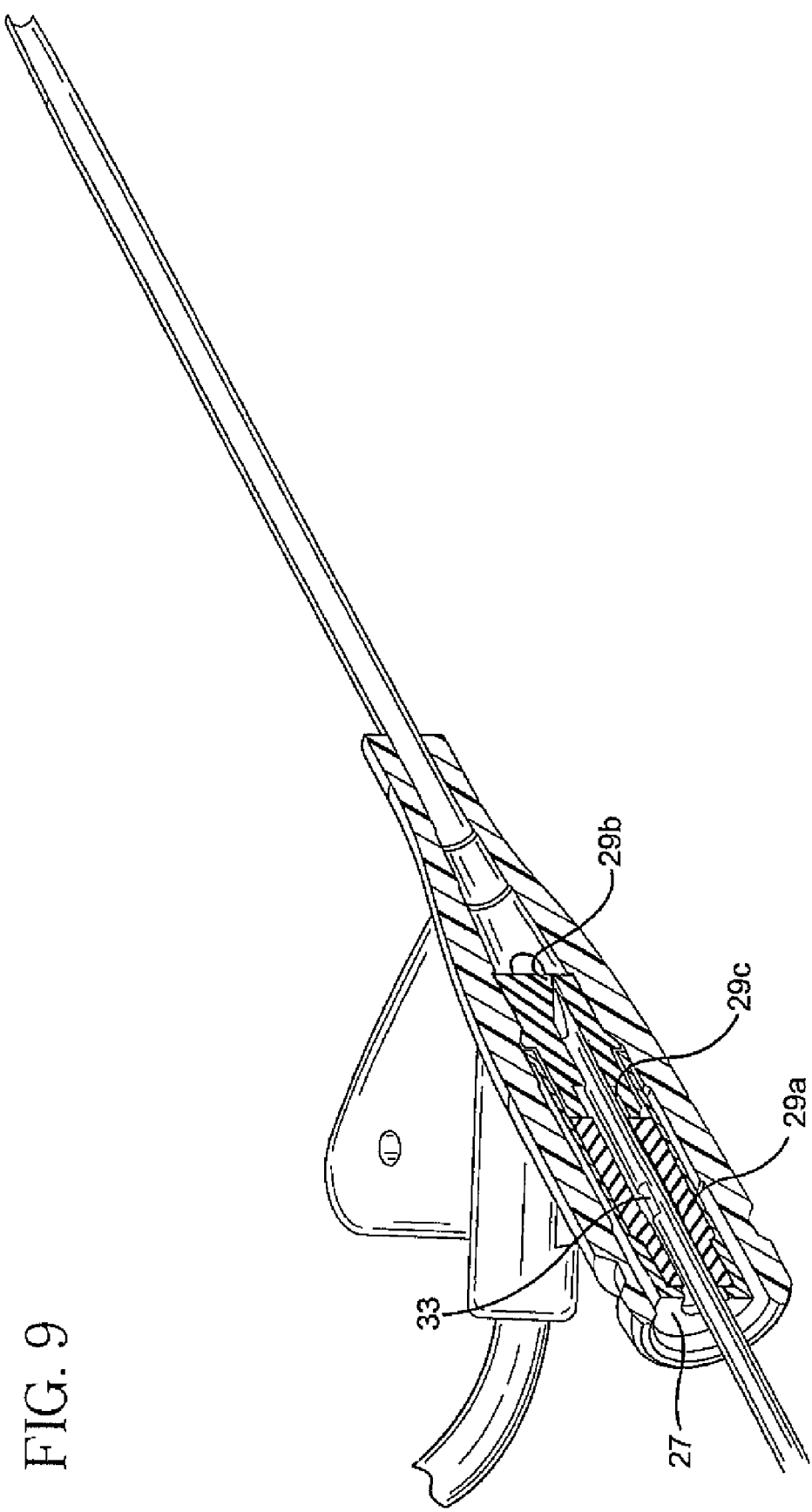
FIG. 9 is a perspective cross-sectional view of the catheter and introducer needle assembly similar to FIG. 4 but showing a different relationship between the introducer needle and the low drag septum where the distal tip of the introducer needle is disposed in the distal portion of the septum.
Figure 10:
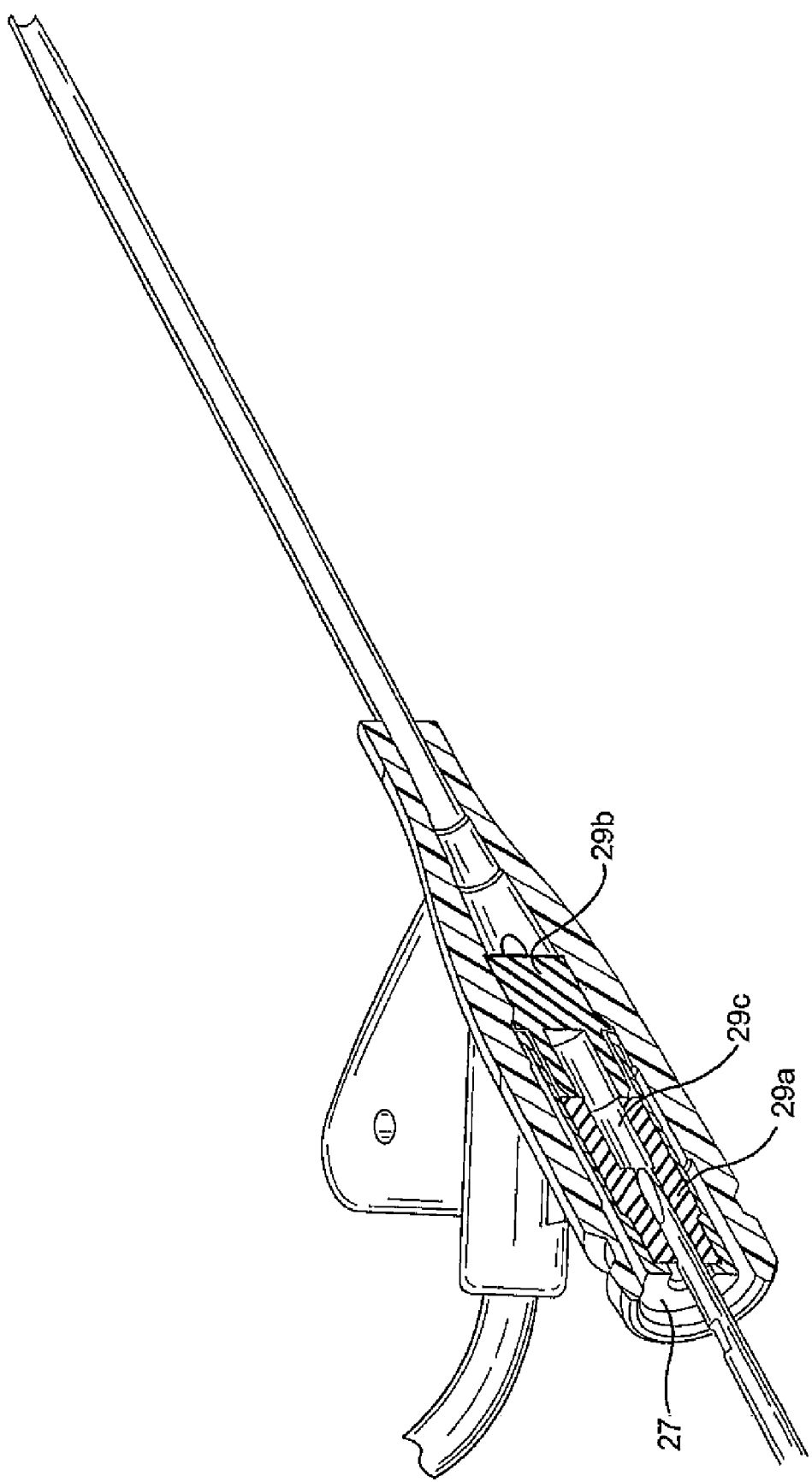
FIG. 10 is a perspective cross-sectional view of the catheter and introducer needle assembly similar to FIG. 5 but showing a different relationship between the introducer needle and the low drag septum where the distal tip of the introducer needle is disposed in the proximal portion of the septum.

In certain implementations of the invention, the septum 29 is longer than the distance between the distal end of introducer needle 31 and the proximal end of notch 33. This prevents fluid or blood from leaking out of catheter assembly 20 when introducer needle 31 is being withdrawn therefrom. As shown in FIG. 8, during withdrawal of introducer needle 31, when the distal end of introducer needle 31 is distal of septum distal portion 29b and notch 33 is located in hollow interior portion 29c anesthesia fluid can flow into introducer needle 31 and into hollow interior portion 29c but anesthesia fluid or blood cannot flow out of catheter assembly 20 because of the proximal portion of septum proximal portion 29a. As shown in FIG. 9, during withdrawal of introducer needle 31 when the distal end of introducer needle 31 is located in the distal portion of septum distal portion 29b, there is no longer a fluid flow path through introducer needle 31 and thus fluid cannot escape from catheter assembly 20. Finally, as shown in FIG. 10, continued withdrawal of introducer needle 31 allows the proximal portion of septum proximal portion 29a to wipe introducer needle 31 of any residual fluid that may be disposed thereon.

Figure 4:
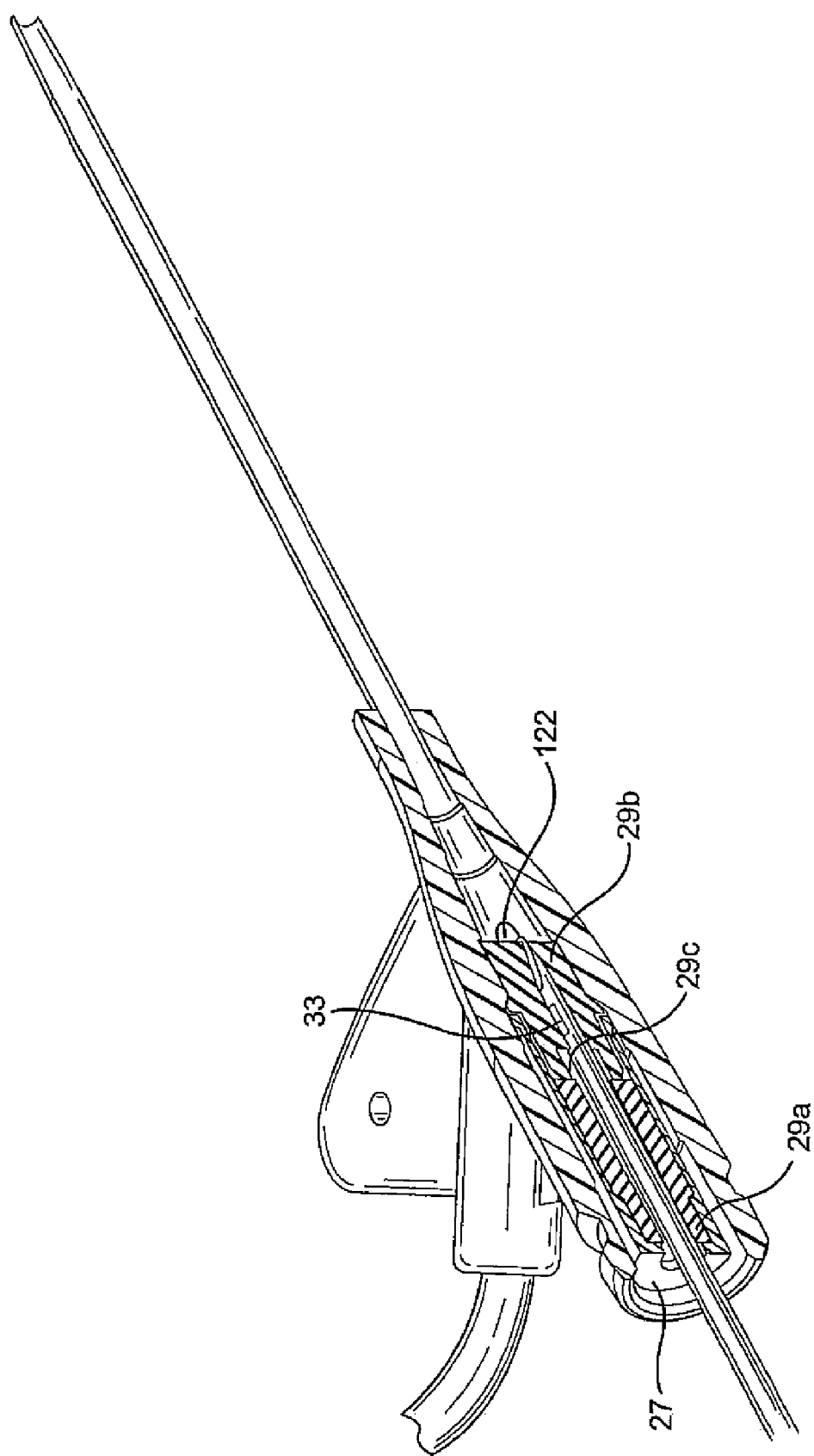
FIG. 4 is a perspective cross-sectional view similar to the view of FIG. 3 after the catheter assembly has been inserted into a patient but before the introducer needle has been completely retracted from the catheter assembly with the distal portion of the introducer needle disposed in the distal portion of the septum.
Figure 5:
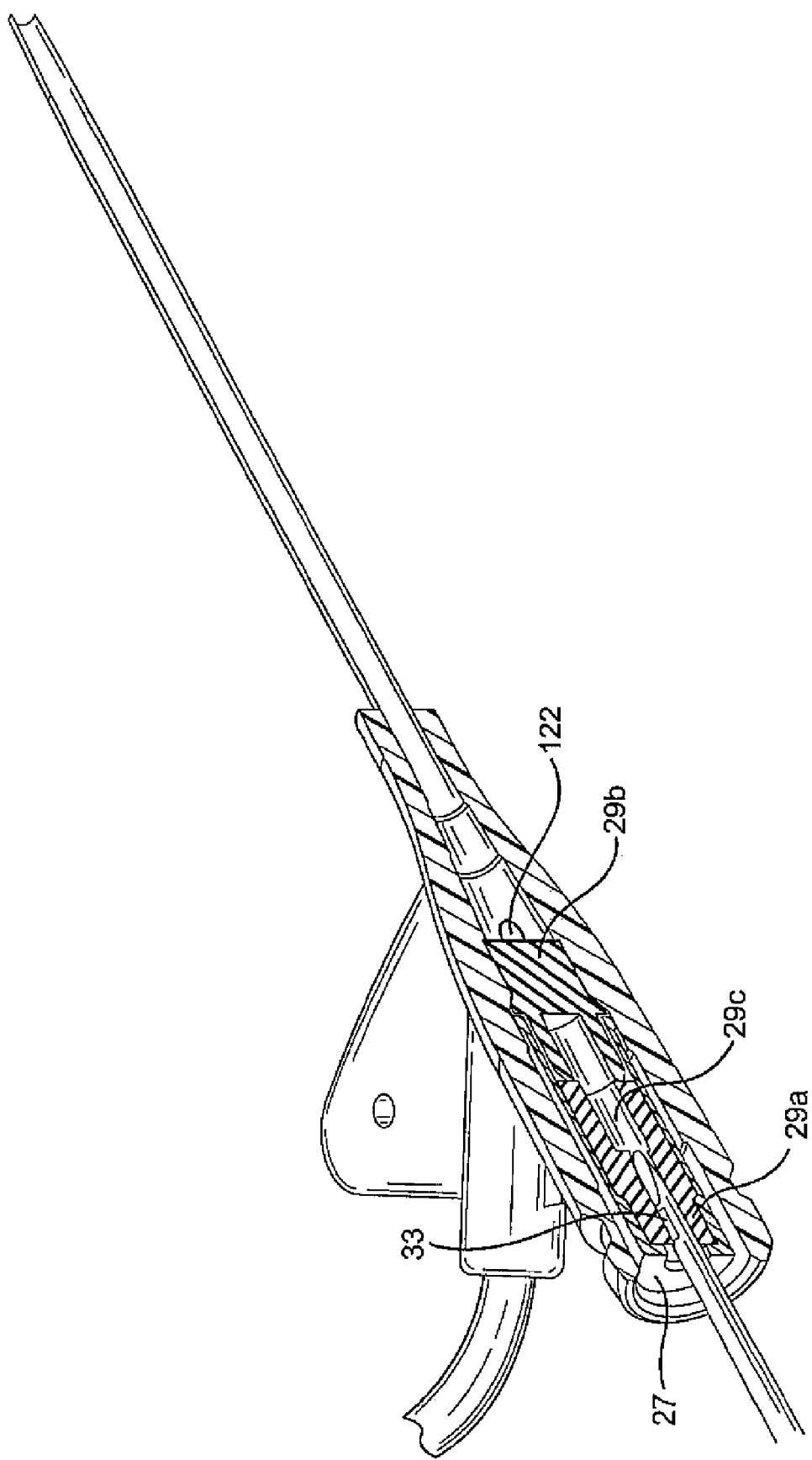
FIG. 5 is a perspective cross-sectional view similar to the view of FIG. 3 after the catheter assembly has been inserted into a patient but before the introducer needle has been completely retracted from the catheter assembly with the distal portion of the introducer needle disposed in the proximal portion of the septum.
Figure 6:
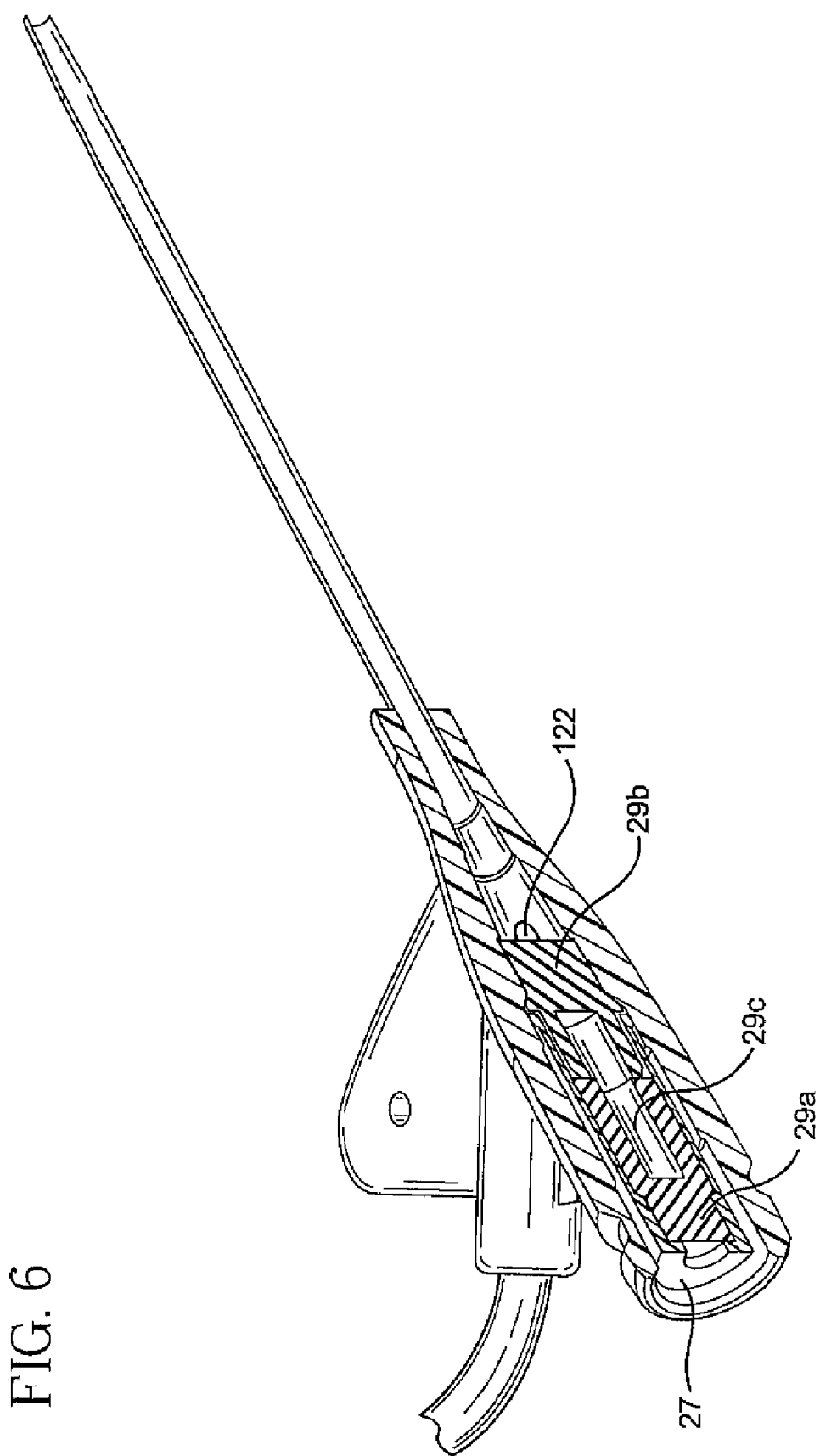
FIG. 6 is a perspective cross-sectional view similar to the view of FIG. 3 after the catheter assembly has been inserted into a patient with the introducer needle completely retracted from the catheter.

Alternatively, the proximal portion of septum proximal portion 29a and the distal portion of septum distal portion 29b could each be at least as long as the distance between the distal tip of introducer needle 31 and the proximal end of notch 33 formed in the sidewall of introducer needle 31. See FIGS. 4 and 5. This dimension ensures that no flow path is created through introducer needle 31 between the proximal and distal sides of either septum distal portion 29b or septum proximal portion 29a. This will thus minimize fluid leakage into hollow interior portion 29c as introducer needle 31 is removed from septum distal portion 29b.

In order to minimize drag on introducer needle 31, the distal portion of septum distal portion 29b and the proximal portion of septum proximal portion 29a should not be longer than about 3 millimeters. Preferably, the distal portion of septum distal portion 29b should be between about 2 and about 3 millimeters long while the proximal portion of septum proximal portion 29a should be between about 1 and about 2.5 millimeters long. In addition, the septum 29 and/or septum housing 27 can include needle capture and shield functionality, which could eliminate the need for a separate needle shield 200 of the type discussed above.

Figure 3:
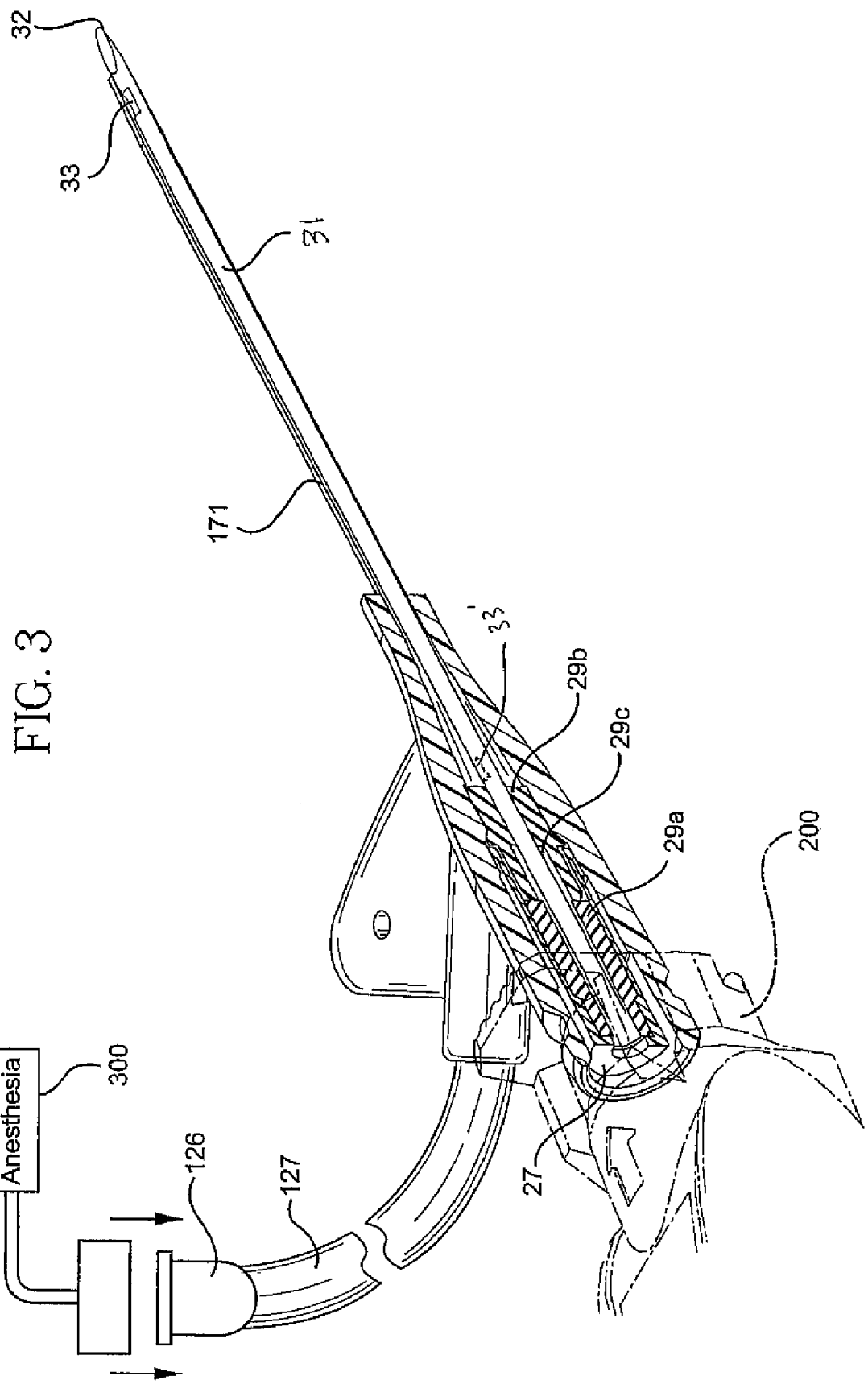
FIG. 3 is a perspective cross-sectional view taken along line 3-3 in FIG. 1 showing the catheter and introducer needle assembly having a first embodiment of the low drag septum, with a portion of the introducer needle assembly in phantom, prior to insertion into a patient.

Introducer needle assembly 30 includes introducer needle 31 having a sharp distal tip 32 defined by a bevel, a central bore 130 and a proximal end connected to a needle hub 34. The needle (excluding the very tip) may be coated with a lubricant that is an electric insulator. Leads 140 may be connected to the needle at its proximal end to allow the delivery of an electrical charge to the needle, as discussed below. The lead 140 may be, welded, crimped or soldered (or a combination of these) to the proximal end of the needle. Alternatively, the leads could be formed integrally with the needle itself, or with a collar in the needle hub in which the needle sits. Further, the leads could be attached to a collar that is within the needle hub and that grips the needle. Introducer needle 31 is preferably formed from stainless steel and has a longitudinal axis that is generally parallel to the longitudinal axis of catheter and introducer needle assembly 10. Introducer needle 31 may be formed with notch 33, i.e., a hole or opening in the sidewall, adjacent to the distal end to allow fluid to flow into the open distal end of introducer needle 31, through the central bore, and then out of notch 33 into the annular space 171 between catheter 21 and introducer needle 31. Alternatively, the notch 33 may be positioned on the needle 31 such that it is aligned with or substantially aligned with opening 122 in the insertion position (see notch 33' as shown, for example, in FIG. 3). In such case, fluid passing through the tube 25 will flow directly through opening 122 into the notch 33', and out of the tip 32 of the needle 31. The tip of the catheter is narrowed to sealingly engage the needle near the tip. As discussed below, the seal will direct fluid flow in the annular space through the notch, rather than out the distal end of the catheter.

A vented plug, which allows air but not fluid to flow there through, may be provided at the fluid access device to permit blood flow into the extension tube 25. Needle hub 34 may be formed from the same types of materials that are used to form catheter adapter 24. Of course, other materials could be used to form needle hub 34.

As will be understood, the instant invention permits the delivery of peripheral block anesthesia via a "closed" system, that is, a system that does not create an open conduit from the environment to the patient's tissue. Such systems are desirable because they can reduce risk of infection. In the implementation of the invention depicted in the Figures, the needle is withdrawn through a septum 29 (thus maintaining system closure), and the anesthesia is introduced through the luer lock adapter 126, which an also be a closed system device such as that disclosed in U.S. Pat. No. 6,171,287 or that depicted in FIGS. 18-22, referenced above.

To use the catheter and needle assembly 10, the clinician first inserts the needle tip 32 into the patient's tissue. Typically, the clinician will use anatomical landmarks to determine where to insert the needle 31. The clinician will also receive tactile feedback from the patient's tissue. For example, if the needle tip is moving adjacent to an artery, the clinician can feel the pulsing blood. Further, the clinician can detect parasthesia should the needle tip actually "hit" the nerve. To assist in locating the needle tip, the clinician can provide an electrical charge, via the leads 140, to the needle 31. Since the catheter 21 is made of an electrical insulating material, the charge on the needle 31 only passes to the patient's tissue at the needle tip. Consequently, the clinician can observe the response of the tissue surrounding the tip, discerning the precise location of the tip within the target tissue.

After confirming placement of introducer needle 31 and catheter 21 in the target tissue, the clinician can then attach a source of anesthesia 300, such as a filled syringe, to the luer lock adapter 126 (this can also be done before insertion of the catheter and introducer needle assembly, as desired by the particular clinician). As the clinician actuates the syringe, anesthesia fluid passes through the extension tube to the catheter adapter 24. When the notch 33 is positioned near the tip 32 of the needle 31, the fluid passes through the annular space 171. The seal formed between the tip of the catheter and the tip of the needle directs the fluid in the annular space through the notch 33 in the needle 31 into the central bore of the needle 31 and out the open tip of the needle 31. When the notch 33' (see FIG. 3) is alternatively positioned in alignment with opening 122 of the adapted 21, the anesthesia fluid passes directly through the notch 33', into the central bore of the needle 31 and out the open tip 32 of the needle 31. Anesthesia is thus delivered through the extension tube to the catheter adapter 26 and out the needle tip 22. The clinician is therefore able to immediately deliver anesthesia to a precise location in the patient's tissue.

Figure 23:
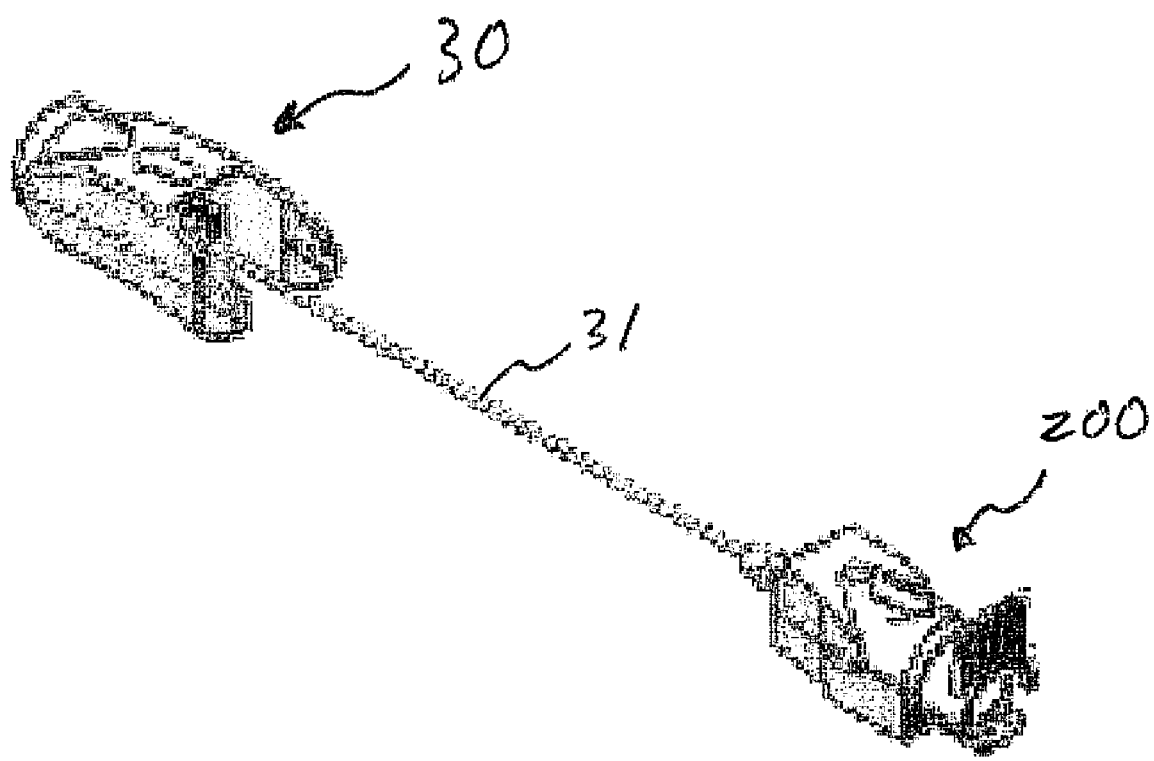
FIG. 23 is a perspective view of an example of the relationship between the needle assembly shown in FIG. 1 and the needle shield assembly when the needle shield assembly is extended over the needle tip.

After this initial introduction of anesthesia, the clinician then withdraws introducer needle 31 from catheter 21 by moving needle hub 34 proximally while holding the catheter adapted 24 in place on the patient. Introducer needle assembly is removed from catheter adapter 24 and disposed of according to the facility's disposal protocol. Again, because of septum 29, blood and liquid anesthesia will not escape from catheter adapter 24 even as the needle is removed. A needle shield 200 may be provided in the assembly. In such case, the tip of the needle 31 will be shielded upon withdrawal as shown in FIG. 23. Further details of the needle shield 200 can be found in U.S. patent application Ser. Nos. 09/590,600 and 09/717,148, and in WO 01/93940, referenced above.

As can be appreciated, during infusion of the anesthetic it is desirable that a clinician be able to aspirate though the device to assure that the needle point 32 is not accidentally located within an artery (which anatomically is very near the target nerves). The need to aspirate is so that a clinician can determine if the device is in the venous system prior to infusing significant amounts of anesthetic, which could result in a very detrimental result if infused into the venous system. If the device accidentally penetrates an artery, during aspiration blood would be drawn through the needle point 32, out through the notch 33 in the needle 31, and visualized in the annular space between the needle 31 and the catheter 21 and all fluid connection locations proximal of the notch 33 (i.e. catheter adapter and extension tubing) if the notch 33 is located near the distal end of the needle. If the notch 33' is located in the catheter adapter 24 the aspirated blood would be visualized in the clear/translucent catheter adapter 24 and points proximal of the notch located within the catheter adapter 24.

The clinician can then bend wings 26 so they match the contour of the patient's skin and suture catheter assembly 20 to the patient's skin using suture holes 28. Alternatively, the clinician can tape catheter assembly 20 to the patient's skin, or use some other method of affixation. The catheter remains within the patient with the tip of the catheter in the tissue to be anesthetized. The clinician can deliver additional anesthesia to the tissue by delivering anesthesia to the luer lock adapter 126 as discussed above.

Another implementation of an aspect of the present invention is shown in FIGS. 14-18. Similar to introducer needle assembly 10 discussed above, the introducer needle assembly 300 comprises a needle assembly 302 and a catheter assembly 304. Needle assembly 302 includes a needle handle 306 having an opening 307 that mates with a bayonet mounting pin 321 on the catheter assembly 304. A needle 308 having a notch 310 and open needle tip 311, and constructed similar to needle 31 discussed above, is mounted in the needle handle 306 by, for example, adhesive or any other suitable mounting material or technique. Alternatively, the notch 310 can be configured as notch 310' shown in FIG. 18 to be positioned at a more proximal location along needle 308 to function in a manner similar to notch 33' discussed above. The needle handle 306 has a rear opening which is capable of receiving an electrical connector assembly 314 that can removably attach to the back of the needle 308. The connector 314 is coupled to a conduit 316 that is further coupled to another connector 318 having an opening that enables the connector 318 to couple to a connector of a power supply (not shown) to deliver current to the needle 308 in a manner similar to that discussed above.

The needle 308 is received into the catheter assembly 304 which includes a catheter 322 into which the needle passes 308, so that an annular space 323 similar to annular space 171 discussed above is formed between the needle 308 and catheter 322. Catheter assembly 304 further includes a side port 330 having an opening 331 configured similar to opening 122 discussed above. The side port 330 is connected to conduit 326 that is further connected to an adapter 324 having an opening 328 therein. Adapted 324 can include a closed-system access port, such as the needleless luer access connector disclosed in U.S. Pat. No. 6,171,287 referenced above and shown in FIGS. 19-22. Catheter assembly also includes a septum 332 and septum housing 334 similar to septum 29 and septum housing 27, respectively, as discussed above. Catheter assembly 304 further includes bayonet mounting pin 321 that is received and mates with opening 307 in needle handle 306 to removably secure needle handle 306 to catheter assembly 304. Specifically, the bayonet pin 321 enters the opening 307 and becomes snap fit with the catheter adapted 324 by twisting the catheter adapter 324 and needle handle 306 relative to each other about their respective axes, thus securing the catheter adapter 324 to the needle handle 306 so that they do not separate as the clinician is searching for the nerve. That is, in the process of finding the right nerve the clinician may withdraw the needle/catheter multiple times which could cause the catheter adapter 324 to separate from the needle handle 306 allowing the tip of the catheter 322 to extend beyond the needle tip 311. The bayonet pin and slot arrangement secures the two together until the clinician disconnects the two by twisting the bayonet mounting pin 321 past a snap in the needle handle 306 allowing it to come out the slot in the distal end of the handle 306.

The needle 308, catheter assembly 304, catheter 322 and related components are made of materials similar to those discussed above. The introducer needle assembly 300 can thus be used to deliver anesthesia in a manner similar to introducer needle assembly 10 as discussed above.

Although the embodiments of the present invention have been disclosed for illustrative purposes, those skilled in the art will appreciate that various modifications, additions and substitutions are possible, without departing from the scope and spirit of the invention as disclosed in the accompanying claims. For example, while certain aspects of the current invention are depicted in the context of a side ported catheter adapter, it will be appreciated that other ports of catheter adapters and hubs may be employed in conjunction with aspects of the invention. For example, a closed system access port may be used to serve as the septum. The needle would then pass through the access port until removed. Once removed, a luer tip syringe can then access the access port.

What is claimed is:

1. A method for delivering anesthesia including:
providing a needle with a notch, a tip and a central bore passing through the needle and creating a fluid flow path between the notch and the tip, wherein the needle is formed of a material capable of conducting an electrical charge;
providing a catheter having a proximal end and a distal end disposed slidingly about the needle such that an annular space is formed between at least a portion of the needle, the tip of the needle extends out of the distal end of the catheter, and the catheter sealingly engages the needle near the tip distal to the notch;
wherein the needle and catheter form a catheter assembly;
inserting the catheter assembly into tissue to be anesthetized;
delivering an electrical charge to the needle, whereby the tissue in contact with the tip receives the charge; and
delivering anesthesia into the annular space such that anesthesia flows through the annular space, through the notch, through the central bore and out the tip of the needle.

2. The method of claim 1 further including:
withdrawing the needle from the catheter; and
delivering additional anesthesia, at selected times, to the tissue through the catheter.

3. The method of claim 2 wherein a catheter hub is provided connected to the catheter, the method further including affixing the catheter hub to the patient.

4. The method of claim 3 wherein wings are attached to the catheter hub and the hub is attached to the patient by taping at least the wings to the patient's skin.

5. The method of claim 3 wherein an extension tube is attached to the hub, and wherein anesthesia is delivered to the hub via the extension tube.

6. The method of claim 1 wherein the catheter is translucent or transparent.

7. The method of claim 1 wherein the notch is disposed near the tip of the needle within the catheter.

8. The method of claim 1 wherein a catheter hub is provided attached to the catheter and wherein the catheter hub has a side port such that a fluid path is formed between the side port and the catheter.

9. The method of claim 1 wherein the notch is disposed within a catheter adapter.

10. The method of claim 1 wherein the needle, excluding its tip, is coated with a lubricant that is an electrical insulator.

11. A method for delivering anesthesia including:
providing a needle having a notch, a tip and a central bore passing through the needle and creating a fluid flow path between the notch and the tip, wherein the needle is formed of a material capable of conducting an electrical charge;
providing a catheter having a proximal end and a distal end slidingly disposed about the needle such that the tip of the needle extends out of the distal end of the catheter and the catheter sealingly engages the needle near the tip distal to the notch;
providing a closed system access port in fluid communication with the catheter;
wherein the needle and catheter form a catheter assembly;
inserting the catheter assembly into tissue to be anesthetized;
delivering an electrical charge to the needle, whereby the tissue in contact with the tip receives the charge, and;
delivering fluid to the catheter via the closed system access port such that the fluid flows through the notch, through the central bore and out the tip of the needle.

12. A method for delivering anesthesia including:
providing a needle with a notch, a tip and a central bore passing through the needle and operably connecting the notch and the tip;
providing a catheter having a proximal end and a distal end disposed slidingly about the needle such that an annular space is formed between at least a portion of the needle, wherein the tip of the needle extends out of the distal end of the catheter and the catheter sealingly engages the needle near the tip distal to the notch;
wherein the needle and catheter form a catheter assembly;
inserting the catheter assembly into tissue to be anesthetized; delivering an electrical charge to the needle, whereby the tissue in contact with the tip receives the charge; and delivering anesthesia into the annular space such that anesthesia flows through the annular space, through the notch, through the central bore and out the tip of the needle.

13. A method for delivering anesthesia including:

providing a needle with a notch, a tip and a central bore passing through the needle and creating a fluid flow path between the notch and the tip, wherein the needle is formed of a material capable of conducting an electrical charge;

providing a catheter having a proximal end and a distal end disposed slidingly about the needle such that an annular space is formed between at least a portion of the needle, wherein the tip of the needle extends out of the distal end of the catheter and the notch is disposed within the catheter with the catheter sealingly engaging the needle to direct fluid flow in the annular space through the notch rather than out the distal end of the catheter;

wherein the catheter electrically insulates the needle excluding the tip;

wherein the needle and catheter form a catheter assembly;

inserting the catheter assembly into tissue to be anesthetized;

delivering an electrical charge to the needle, whereby the peripheral nerve tissue near the tip receives the charge, thereby exciting the enervated tissue, causing a response and thereby identifying the location of the nerve; and delivering anesthesia into the annular space such that anesthesia flows through the annular space, through the notch, through the central bore and out the tip of the needle.

* * * * *